US010557804B2

(12) United States Patent
Brunner et al.

(10) Patent No.: US 10,557,804 B2
(45) Date of Patent: Feb. 11, 2020

(54) METHOD AND SYSTEM FOR WEAR MONITORING USING RF REFLECTIONS

(71) Applicant: REI, Inc., Salt Lake City, UT (US)

(72) Inventors: Daniel J. Brunner, Salt Lake City, UT (US); Randy Richardson, South Jordan, UT (US); Robert Koontz, Herriman, UT (US); Alex Schumacher, Salt Lake City, UT (US); Jeffrey J. Schwoebel, Park City, UT (US); Randall Johnson, Salt Lake City, UT (US)

(73) Assignee: REI, Inc., Salt Lake City, UT (US)

( * ) Notice: Subject to any disclaimer, the term of this patent is extended or adjusted under 35 U.S.C. 154(b) by 100 days.

(21) Appl. No.: 15/730,465

(22) Filed: Oct. 11, 2017

(65) Prior Publication Data

US 2018/0172605 A1     Jun. 21, 2018

Related U.S. Application Data

(60) Provisional application No. 62/477,228, filed on Mar. 27, 2017, provisional application No. 62/430,400, filed on Dec. 6, 2016, provisional application No. 62/417,763, filed on Nov. 4, 2016, provisional application No. 62/407,095, filed on Oct. 12, 2016.

(51) Int. Cl.
| | |
|---|---|
| *G01N 22/02* | (2006.01) |
| *B60C 25/00* | (2006.01) |
| *B60C 25/05* | (2006.01) |
| *B65G 43/00* | (2006.01) |
| *F16H 57/01* | (2012.01) |
| *B66B 7/12* | (2006.01) |

(52) U.S. Cl.
CPC ............ *G01N 22/02* (2013.01); *B60C 25/007* (2013.01); *B60C 25/0551* (2013.01); *B65G 43/00* (2013.01); *B66B 7/1215* (2013.01); *F16H 57/01* (2013.01); *F16H 2057/014* (2013.01)

(58) Field of Classification Search
CPC ..... G01N 22/02; B60C 11/243; B60C 11/246; B60C 25/007; B60C 23/06; F16H 57/01; B65G 43/00; B65G 43/08
See application file for complete search history.

(56) References Cited

U.S. PATENT DOCUMENTS

| 5,406,842 A * | 4/1995 | Locke ................... G01F 23/284 |
| | | 324/643 |
| 7,095,311 B2 * | 8/2006 | Coates ............... G06K 19/0672 |
| | | 340/10.1 |

(Continued)

OTHER PUBLICATIONS

Young, Lee W., "International Search Report and Written Opinion", prepared for PCT/US17/56185, dated Nov. 30, 2017, 13 pages.

*Primary Examiner* — Jeff W Natalini
(74) *Attorney, Agent, or Firm* — Winstead PC

(57) ABSTRACT

In an embodiment, a system for wear monitoring, includes a wear surface, a metallic reflector embedded in the wear surface, a radio-wave transmitter, and a radio-wave receiver. The metallic reflector reflects radio waves transmitted by the radio-wave transmitter for detection by the radio wave receiver. Attenuation of the radio waves between transmission by the radio-wave transmitter and detection by the radio-wave receiver indicates a degree of wear of the wear surface.

19 Claims, 21 Drawing Sheets

(56) References Cited

U.S. PATENT DOCUMENTS

| | | | |
|---|---|---|---|
| 7,180,409 B2* | 2/2007 | Brey | B60C 11/24 |
| | | | 116/208 |
| 9,718,315 B2* | 8/2017 | Peine | B60C 23/0408 |
| 2004/0252072 A1 | 12/2004 | Adamson et al. | |
| 2004/0262132 A1 | 12/2004 | Pauley et al. | |
| 2005/0110614 A1 | 5/2005 | Coates et al. | |
| 2006/0042734 A1 | 3/2006 | Turner et al. | |
| 2007/0175555 A1 | 8/2007 | Myatt | |
| 2009/0072958 A1* | 3/2009 | Hammerschmidt | |
| | | | B60C 23/0483 |
| | | | 340/447 |
| 2013/0061971 A1 | 3/2013 | Chamberland | |
| 2014/0360256 A1 | 12/2014 | Orlewski | |

* cited by examiner

METHOD AND SYSTEM FOR WEAR MONITORING USING RF REFLECTIONS

CROSS-REFERENCE TO RELATED APPLICATIONS

This application claims priority to, and incorporates by reference for any purpose, U.S. Provisional Patent Application No. 62/407,095, filed on Oct. 12, 2016, U.S. Provisional Patent Application No. 62/417,763, filed on Nov. 4, 2016, U.S. Provisional Patent Application No. 62/430,400, filed on Dec. 6, 2016, and U.S. Provisional Patent Application No. 62/477,228, filed on Mar. 27, 2017.

TECHNICAL FIELD

The present disclosure relates generally to surface wear monitoring and, more particularly, but not by way of limitation, to sensors and antennas embedded in equipment having wear surfaces for wear monitoring. In one embodiment, the disclosure further relates to methods and systems for providing wear, tear, or rupture status of equipment and items having wear surfaces such as, for example, conveyor belts and tires. In a further embodiment, the disclosure relates to the use of RF reflectors embedded in a belt or tread of a tire and positioned in such a way as to be impacted by wear while reflecting RF radio waves from an RF radio wave transmitter to a radio wave receiver.

BACKGROUND

Every tire and belt has a means to adapt to host equipment and a life-cycle that starts when the belt or tire is installed and ends when wear-out limits are reached. If the belts or tires are worn beyond the wear-out limits or damaged, the host may be damaged or become unsafe. As belts or tires are used, it is normal for overall belt or tire performance to change. In addition, irregular belt or tire-tread wear may occur for a variety of reasons that may lead to replacing a belt or tire sooner rather than later. Regular monitoring of wear condition of belts and tires not only provides an indication of when it is time to replace the belt or tires, it can also help detect other needed maintenance and get the most value out of the equipment. Presently, monitoring of belt and tire wear is performed manually. What is needed is a method and system that provides automated status updates relative to wear, tear, or rupture status of equipment and items having wear surfaces such as, for example, belts and tires.

SUMMARY

Exemplary embodiments disclose a method and system for providing automated status updates relative to wear, tear, or rupture status of equipment having wear surfaces such as, for example, belts and tires. In one embodiment specifically set forth herein, a metallic reflector embedded in the belt or tread of a tire and positioned in such a way as to reflect RF radio waves from an RF radio wave transmitter and focus the reflections to a radio wave receiver.

BRIEF DESCRIPTION OF THE DRAWINGS

For a more complete understanding of the present disclosure and for further objects and advantages thereof, reference may now be had to the following description taken in conjunction with the accompanying drawings in which.

Radio Frequency Reflection for Non-Ferrous Material Wear Sensing

The following background is presented for a better understanding of the principles of the present disclosure. At lower power frequencies, the effects of ground (such as the surface of the Earth) interact with RF signals to bend their course of travel. This bending effect allows lower-frequency RF signals, such as those used in radio and television, to follow the contours of the Earth such as, for example, bending along hills and valleys. As the frequency of the RF signals increase, such as, for example, in the case of microwave signals, this ground effect is less predominant and the signals follow straight courses, regardless of the presence of ground objects. Because these signals follow straight lines, they may be blocked by objects such as buildings, hills, or other structures. At these higher frequencies, these signals are referred to as line-of-sight signals.

Figure 1:
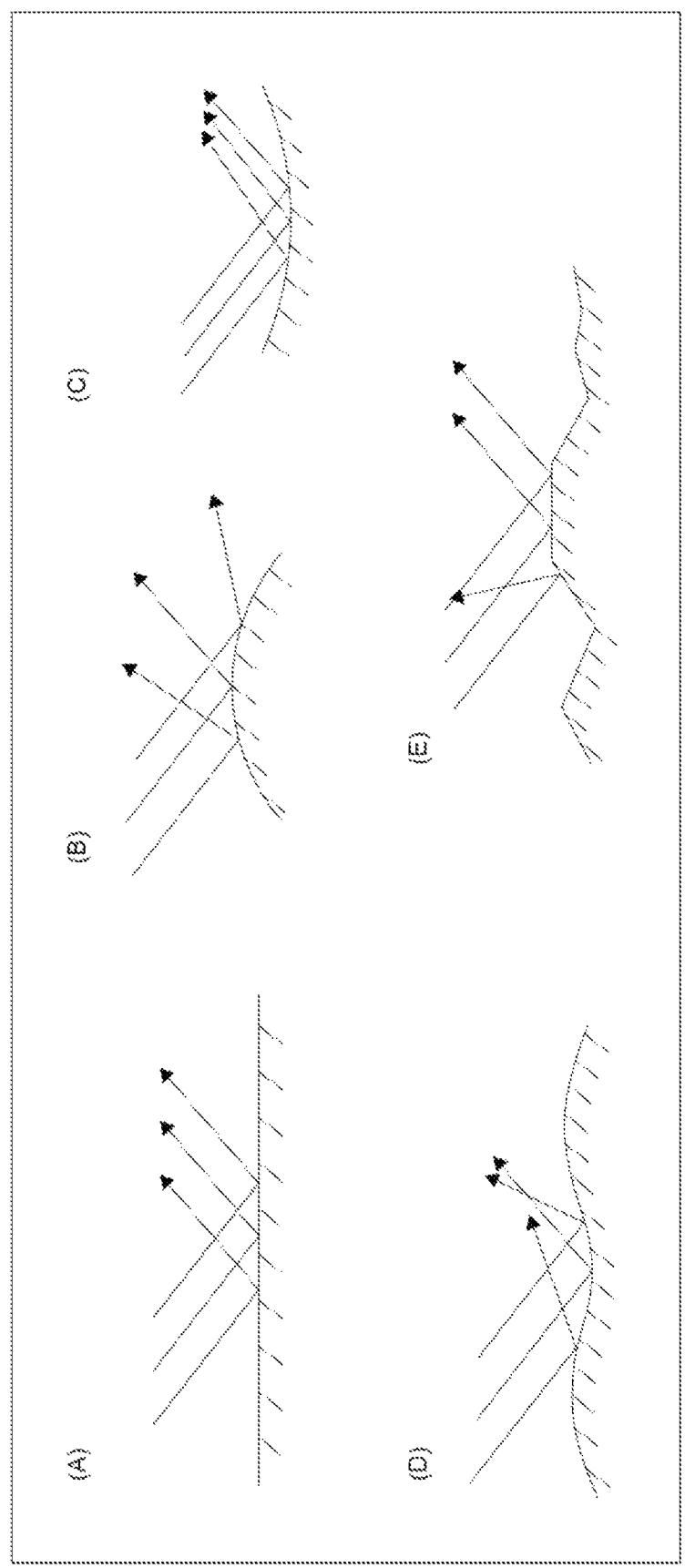
FIG. 1 illustrates reflections of RF energy from various types of surfaces.

When RF signals contact metallic surfaces, part of the signal energy is absorbed into the structure and part is reflected. RF energy that is absorbed is lost in the surface in the form of heat. Incident waves are redirected relative to the angle they strike the surface. Metallic surfaces can generally be classified as being: flat, convex or concave curved or rounded or flattened irregular. FIG. 1 depicts the reflections of the RF energy for the various types of surfaces: (A) flat, (B) convex curved and (C) concave curved, (D) irregular curved and (E) irregular flat surfaces.

Figure 2:
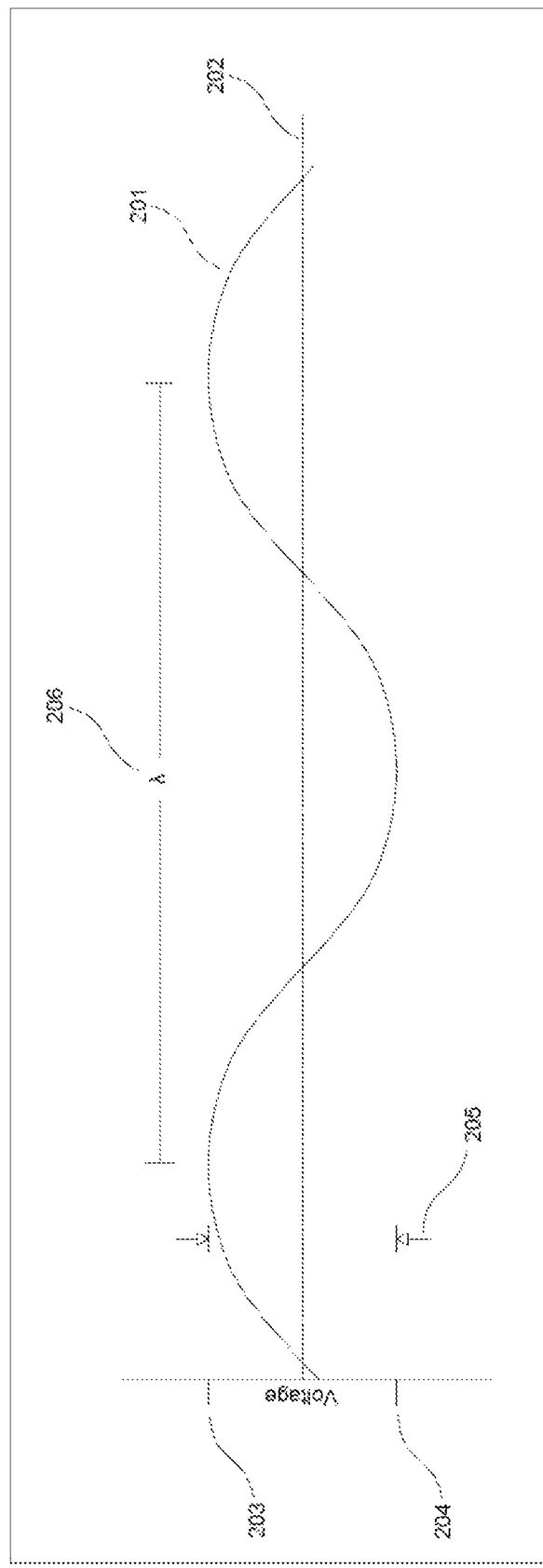
FIG. 2 illustrates a sinusoidal pattern of electrical potential of an RF signal.

As RF signals travel, the electrical potential of the signal varies in a sinusoidal pattern as depicted in FIG. 2. The signal voltage (V) 201 oscillates about a voltage reference point $V_{REF}$ 202 (may be zero volts). The number of times the signal crosses this reference level in the same direction (either positive or negative-going, but not both) each second defines the frequency ($f$) in hertz (Hz). Voltage levels are the positive peak voltage ($V_P$) 203, the negative peak voltage ($-V_P$) 204 and the peak-to-peak voltage ($V_{P-P}$) 205. Since, in a vacuum, RF signals propagate at the speed of light (c), the wavelength ($\lambda$) 206 is defined as the speed of light divided by the signal frequency ($\lambda=c/f$). The term signal amplitude generally refers to the level (positive and/or negative) that the signal deviates from $V_{REF}$.

Addressing now Applicant's approach to utilizing RF reflections for wear monitoring, specific technical aspects are herein presented. Due to physical, cost and regulatory constraints, there is a range of RF frequencies that are effective for monitoring wear. Low frequencies have large wavelengths. These force reflectors to be very large for reasonable signal strength. This adds to cost and may make implementation physically impossible. High frequency RF signals are costly to generate and are not commonly used in other applications. Government regulations may also impact the frequencies that are chosen. Currently low cost RF components are not readily available above 20 GHz ($\lambda$=15 mm). RF wavelengths below 1 GHz ($\lambda$>300 mm) are physically harder to implement. Government regulations such as FCC (United States), CE (Europe), etc. limit the frequencies and amplitudes that may be used without a license. Applicants have observed that signals in the 1 GHz to 20 GHz range exhibit line-of-sight characteristics and could be useful for wear monitoring because reflections will be linear. Signals greater than 20 GHz could also be useful when the technology is readily available. As less expensive and higher frequency components are developed, it is desirable to use these due to their smaller wave lengths.

The use of RF signals to monitor the wear in various components such as tires, conveyor belts, slurry pipe liners and haul truck bed liners etc. rely on the general behaviors of RF signals described above. Specific implementations of these concepts will be described in detail below. The general concept that makes use of RF signals for monitoring is described here. When referring to the types of reflections listed above, Applicants will generally relay on flat, concave and irregular surfaces. These break down into general application types as follows:

Stationary Sensors and Moving Reflectors: Conveyor and drive belts are a good example of this. The RF transmitter and receiver are mounted at a fixed vantage point with the belts having embedded reflectors moving past them.

Figure 3A:
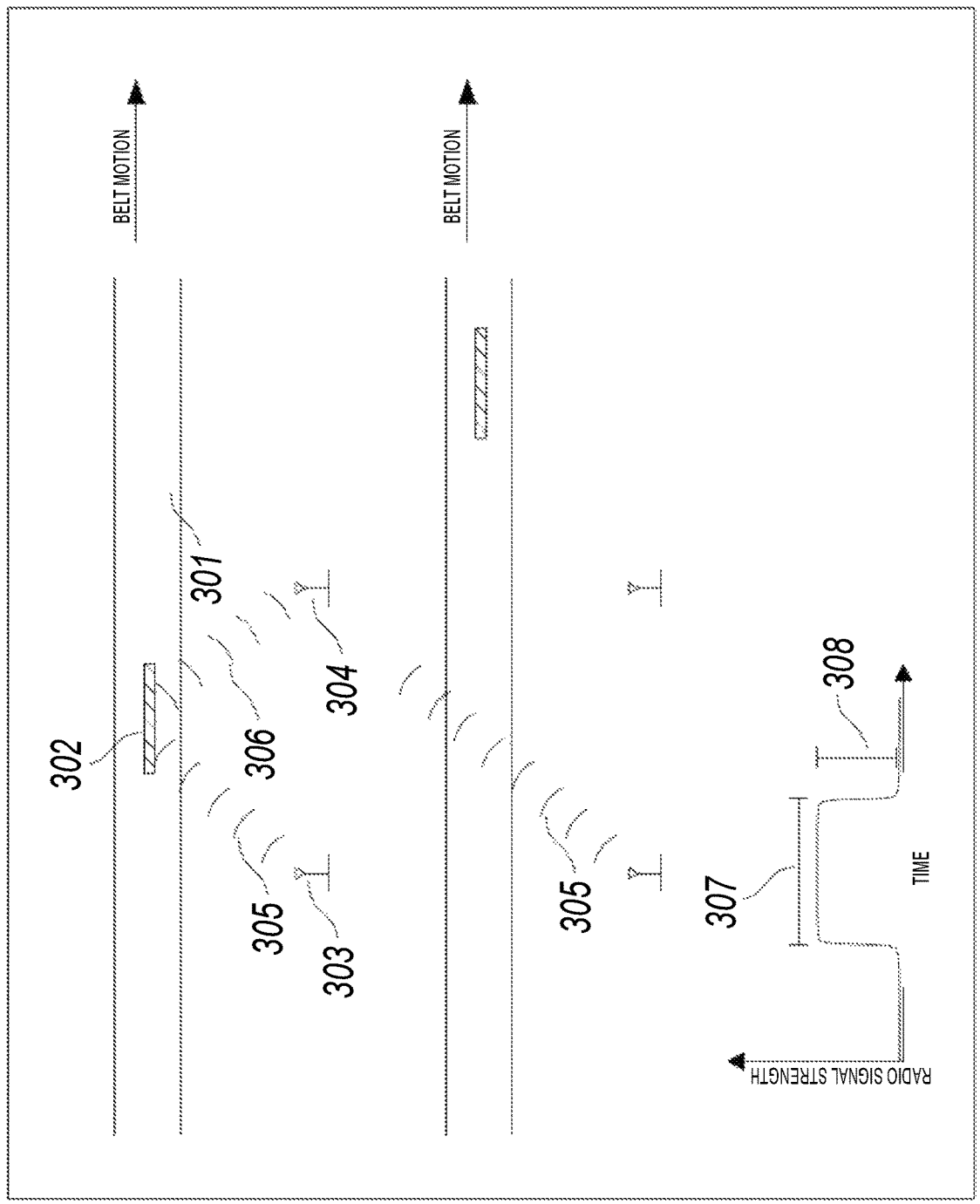
FIG. 3A-3B illustrate a wear monitoring system having reflectors embedded into the device being monitored in accordance with an exemplary embodiment.
Figure 3B:
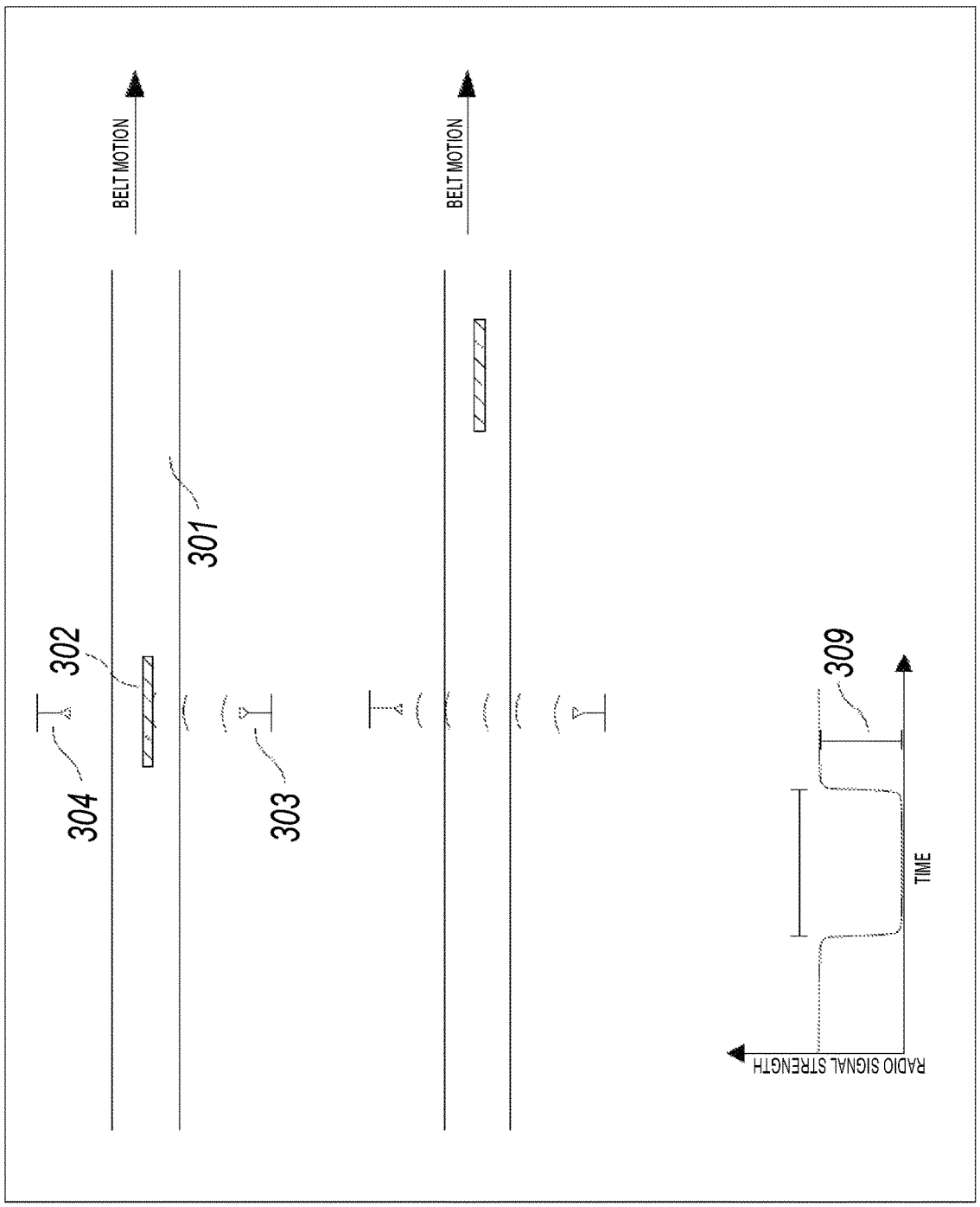

Wear monitoring is least complicated when RF reflecting structures are not present. FIG. 3A and FIG. 3B show examples of wear monitoring where the reflectors are embedded into the device being monitored for wear 301. The device being monitored will be referred to as a belt. As the embedded reflector 302 passes over the antennas 303 and 304, the transmitted signal 305 is reflected 306 back into the receiver 304, as shown in FIG. 3A. When the reflector 302 is past the sensors, the RF wave passes through the belt 301 and no signal is received. When the wear reaches the sensor it will begin to be worn away and the pulse width 307 and amplitude 308 of the received signal will diminish. As shown in FIG. 3B, the receiver 304 may alternatively be positioned on the opposite side of the belt 301. In this embodiment, the presence of the reflector 302 is detected by a drop in the signal of amplitude 309. Placing embedded reflectors at different levels allows multiple wear depths to be monitored. Placing reflectors in patterns will allow position of the belt to be determined.

Figure 4:
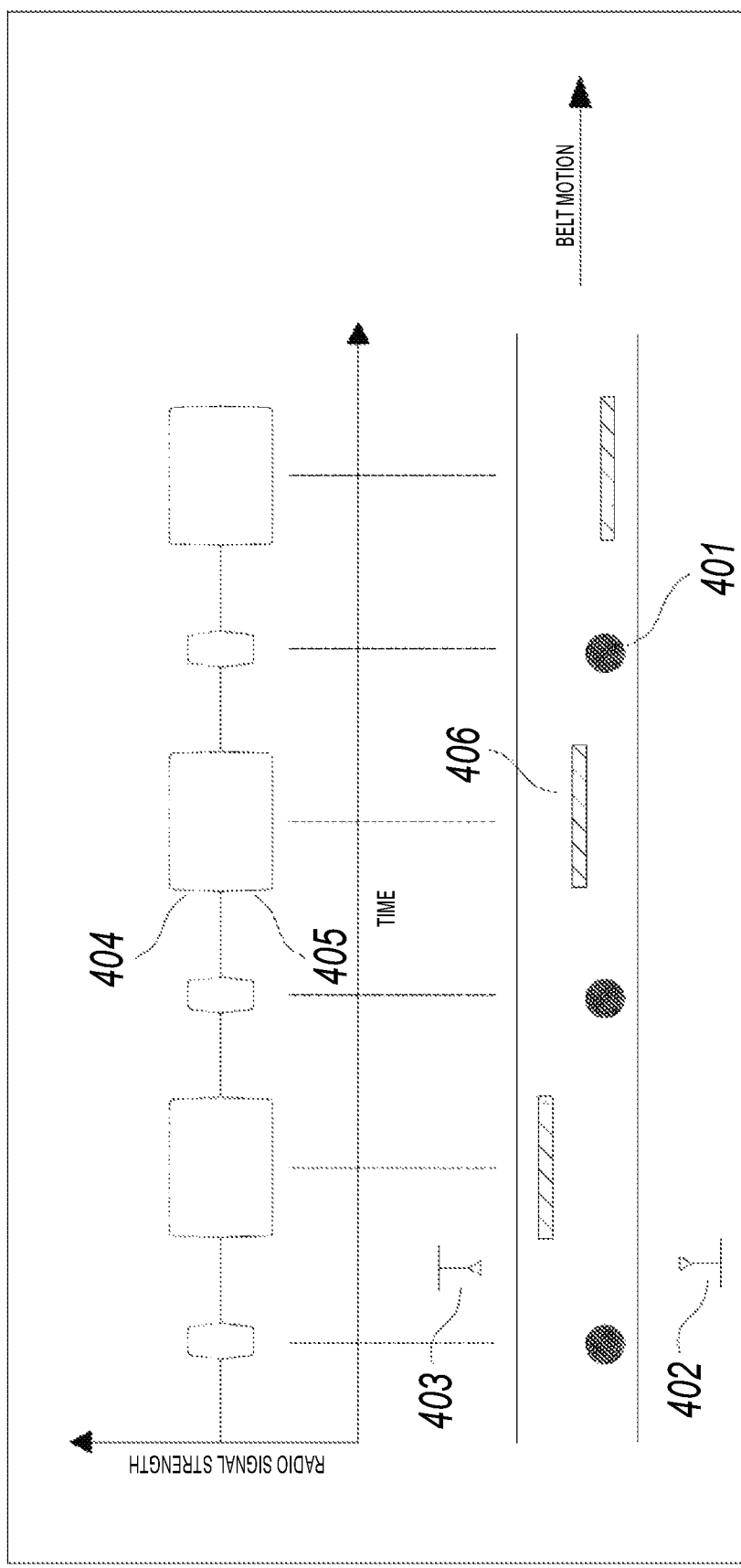
FIG. 4 illustrates a conveyor system having steel cables embedded therein in accordance with an exemplary embodiment.

Applications with embedded structural components that reflect RF. Good examples of this are conveyor belts with embedded steel cables and/or steel mesh to add structural strength:

The addition of reflective structural components adds complexity to the monitoring, but it also adds more information to the signal. First, consider the case where steel cables are embedded at regular intervals to strengthen a conveyor belt. FIG. 4 shows this example. Because the cables 401 are made up of multiple strands of steel wires and the general shape of the cable is convex with respect to RF signal reflections, most of the signals will not be reflected to the receiver as the cable 401 passes over the transmitter 402 and receiver 403 pair. The reflections from the cables will form small signal levels at the receiver. Depending on whether the antenna orientation corresponds to that of FIG. 3A or that of FIG. 3B, the strength of signal received by the receiver will either increase 404 (FIG. 3A orientation) or decrease 405 (FIG. 3B orientation) as the reflectors 406 and cables 401 pass over the antennas. These signals can be processed by the system to determine the speed and relative position of the belt. In this case, the longer pulses correspond to the wear depth reflectors and the shorter pulses correspond to the cables 401.

Figure 5:
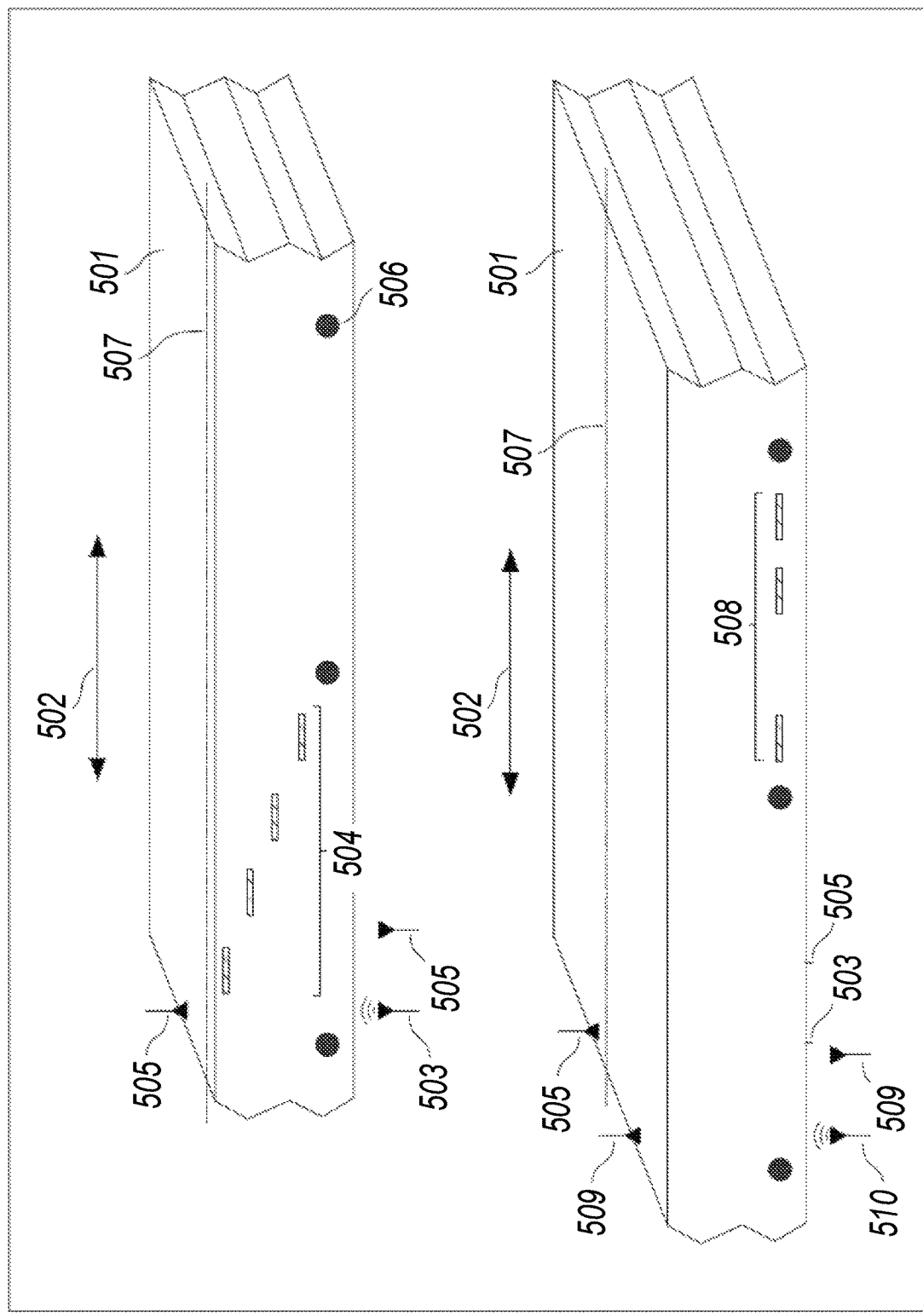
FIG. 5 is a cross-sectional view of a steel cord conveyor belt system in accordance with an exemplary embodiment.

Consistent with the above, there is now shown and described Applicant's approach of wear monitoring for conveyor belts and the like. In one embodiment, the present method and system may be installed on and with conveyor belt systems, as illustrated in FIG. 5. Installation may take place during the belt manufacturing process or in the field as an aftermarket component of the belt. Several radio reflectors, metallic mesh or metallic belt fabric is set at predetermined depths into the belt 501, along all or some of its width and in an orientation perpendicular, parallel, or oblique to belt movement 502. A transmitter 503 conveys radio waves that reflect off of the metal strips 504. The direct or reflected (depending again on FIG. 3A or FIG. 3B orientation) radio waves are collected by at least one radio receiver 505 located as to receive reflected radio waves from the transmitter. The radio receivers 505 are capable of measuring antenna gain. The characteristics of the radio signal collected by the receiver(s) 505 are altered if wear or damage removes any of the metal strips 504 embedded in the belt or if the belt rapidly changes in lateral position (tracking). If excessive wear, damage, or incorrect positioning of the belt is detected, an alarm can be sent to an operator or the belt may automatically be shut off. Steel cord 506 may run laterally and/or longitudinally through standard belts at regular intervals. In various embodiments, monitoring reflections from theses reinforcing wires allows for calculation of belt speed. Metal strips may also be embedded in the belt at a depth and or distance from the centerline 507 unlikely to wear or be damaged in different patterns 508. The shape of radio signal vs. time curve collected by the receiver 509 from the transmitter 510 is a unique identification code to different points along the belt. These identification reflectors are not continuous in the direction of belt movement and may have unique dimensions within a single identification code. This may be used to pinpoint localized damage and/or clock belt velocity. With belt velocity, the reflections from two points can be used to determine the distance between those two points and belt stretch may be determined. Determining stretch across a spliced section of belt allows monitoring the splice's integrity and can be accomplished with this disclosure as previously described. Belt velocity can be compared to the tangential velocity of a pulley, which is related to its angular velocity and radius, or idler roller to determine belt slippage and pulley or idler roller wear. Wear of the belt is expected to be greater near the middle of the belt so identification codes should be embedded near the edge of the belt, and wear reflectors near the centerline 507 of the belt 501. The explicit orientation of the transmitter and receiver array does not need to be uniquely specified given that the wear monitoring system may function successfully as described with the transmitter 503 or 510 and receiver 505 or 509 in many different relative positions and orientations, such as the orientations shown in FIG. 3A and FIG. 3B.

Figure 6:
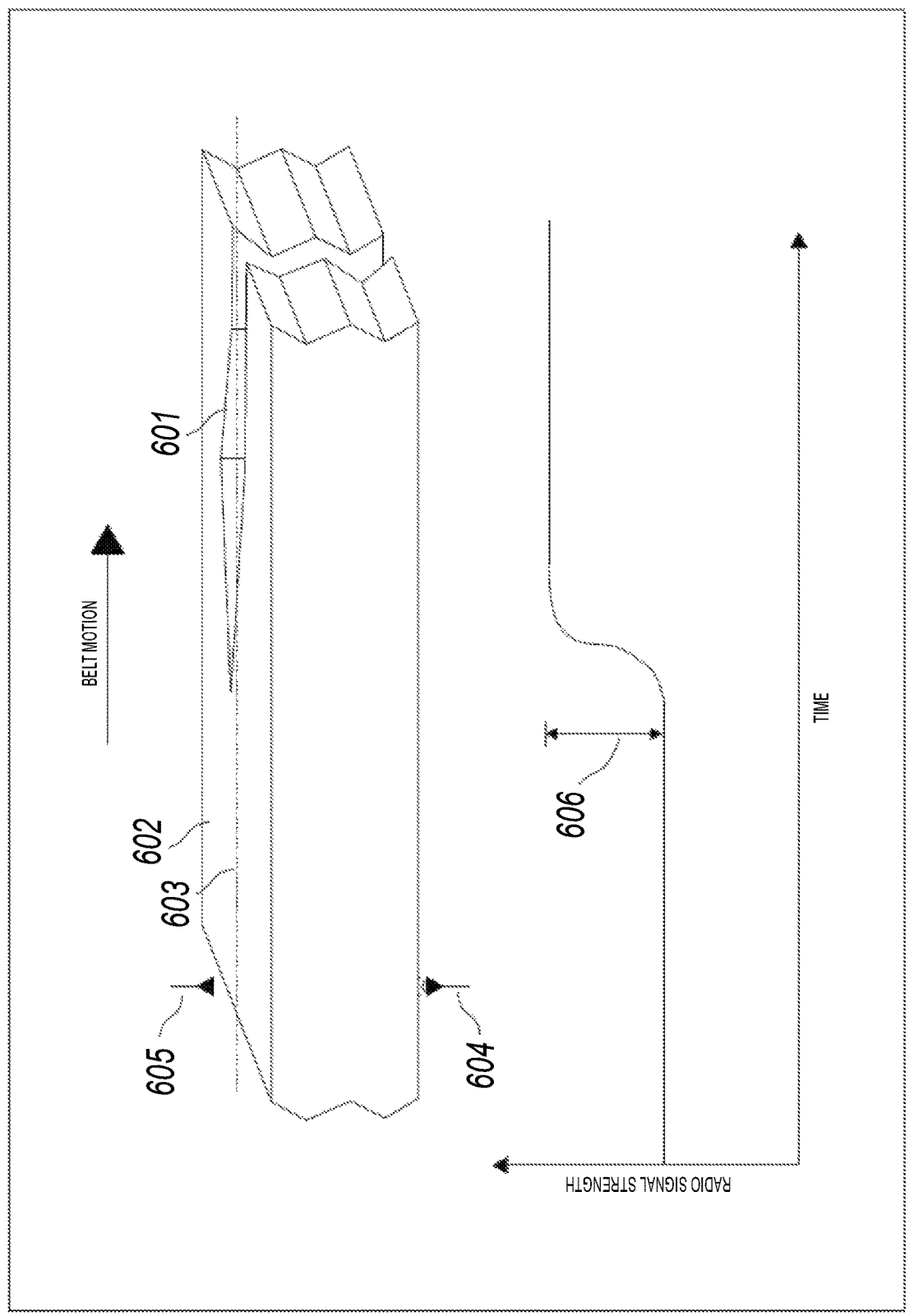
FIG. 6 is a cross-sectional view of a torn conveyor belt system in accordance with an exemplary embodiment.

In the orientation of FIG. 3B, characteristics of the received radio signal may also be altered if damage occurs to the belt but not reflectors. This is because the rubber material of the belt attenuates the radio signal to some degree. In FIG. 6 for example, if a tear 601 in the belt 602 occurs along a path 603 that is monitored by the transmitter 604 and receiver 605, some of the transmitted radio signal will pass through the open space of the tear 601 with little attenuation and the receiver 605 will realize an increase in signal strength 606.

Figure 7:
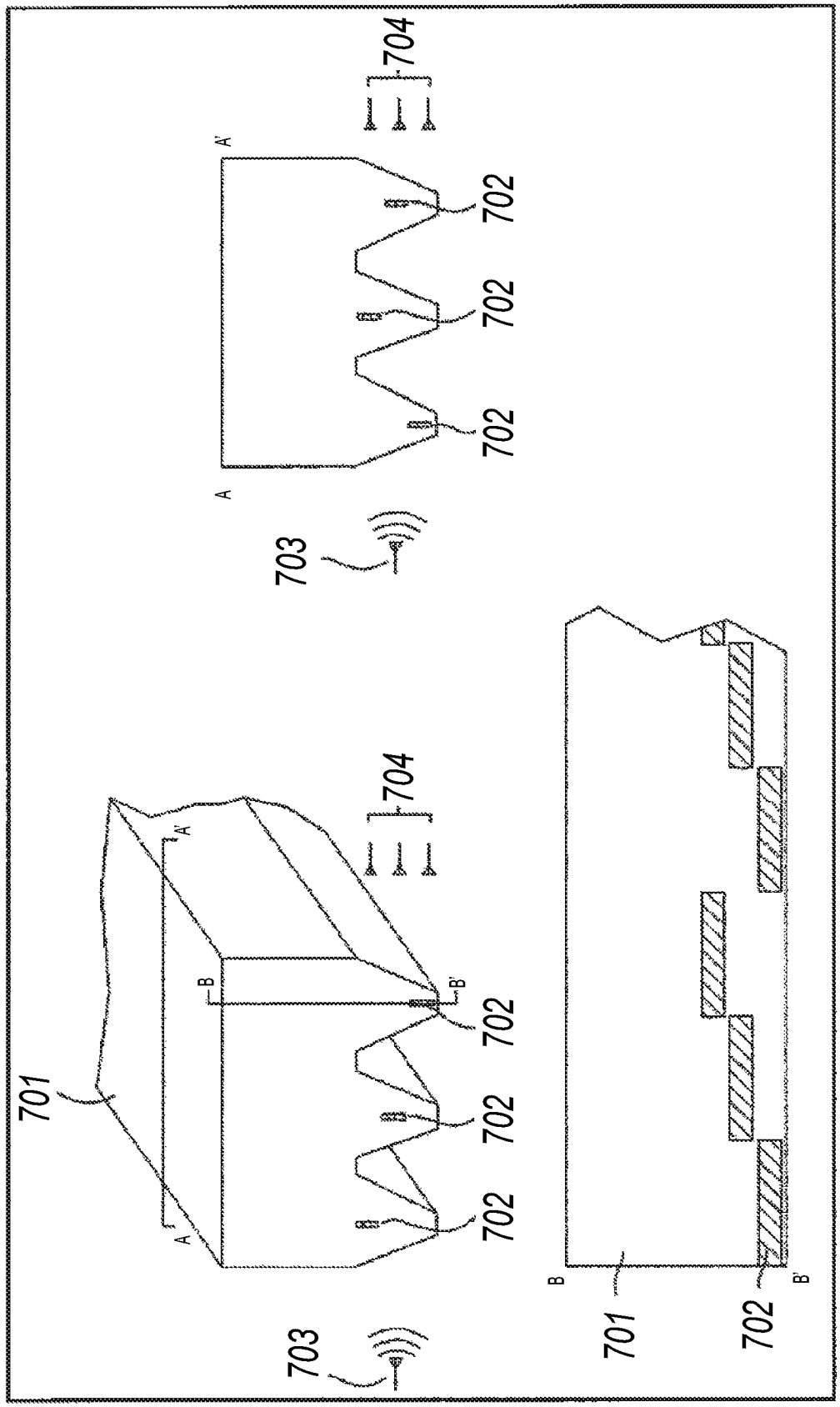
FIG. 7 illustrates front and side views of a serpentine belt monitoring system in accordance with an exemplary embodiment.

FIG. 7 illustrates an embodiment of the disclosure that is embedded in a multi-rib serpentine belt 701. Metal reflectors 702 are solid or mesh and are embedded at predetermined depths in the ribs of the belt 701. If a mesh is used, the mesh spacing must be less than ¼ of the radio transmitter wavelength in order to effectively reflect radio waves. The reflectors are staggered in such a way (see A-A' and B-B') that a side view of the belt would appear to show continuous lengths of metal reflectors along the belt. Staggering the reflectors allows the radio transmitter 703 signal received by receiver array 704 to be representative of the condition of multiple belt ribs at any given time. Staggering the reflectors 702 also allows the belt 701 to be more flexible than if reflectors 702 were continuous along the entire length of the belt 701. Decreased attenuation of the radio signal is indicative of rib damage or wear.

Figure 8:
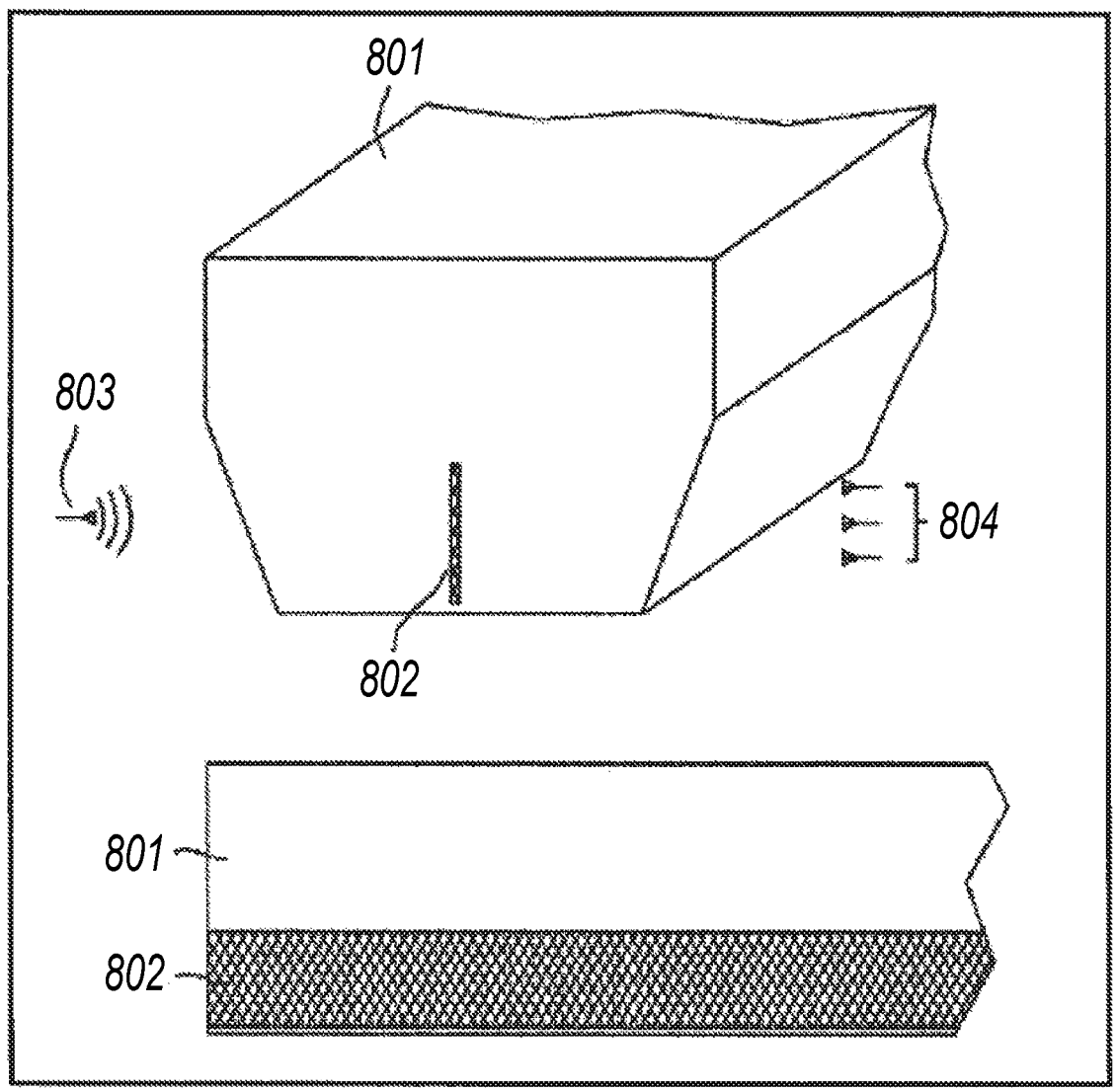
FIG. 8 illustrates front and side views of a v-belt monitoring system in accordance with an exemplary embodiment.

Some belts 801 may only be made with only one rib, as shown in FIG. 8. With such belts, it is an option to embed a single reflector 802 (mesh) along the length of the belt 801. It is also possible to stagger reflectors 802 along the width and length of the belt, as illustrated in FIG. 7. The same transmitter and receiver configuration as previously described for FIG. 7 may be used with single rib, v-belts.

Relatively Stationary Sensors and Reflectors: Tires are a good example of this. The RF transmitter, receiver and reflector all move together as a single unit within the tire as it rotates. When the sensor is required to move with the reflector, the signals only change as wear occurs.

Figure 9:
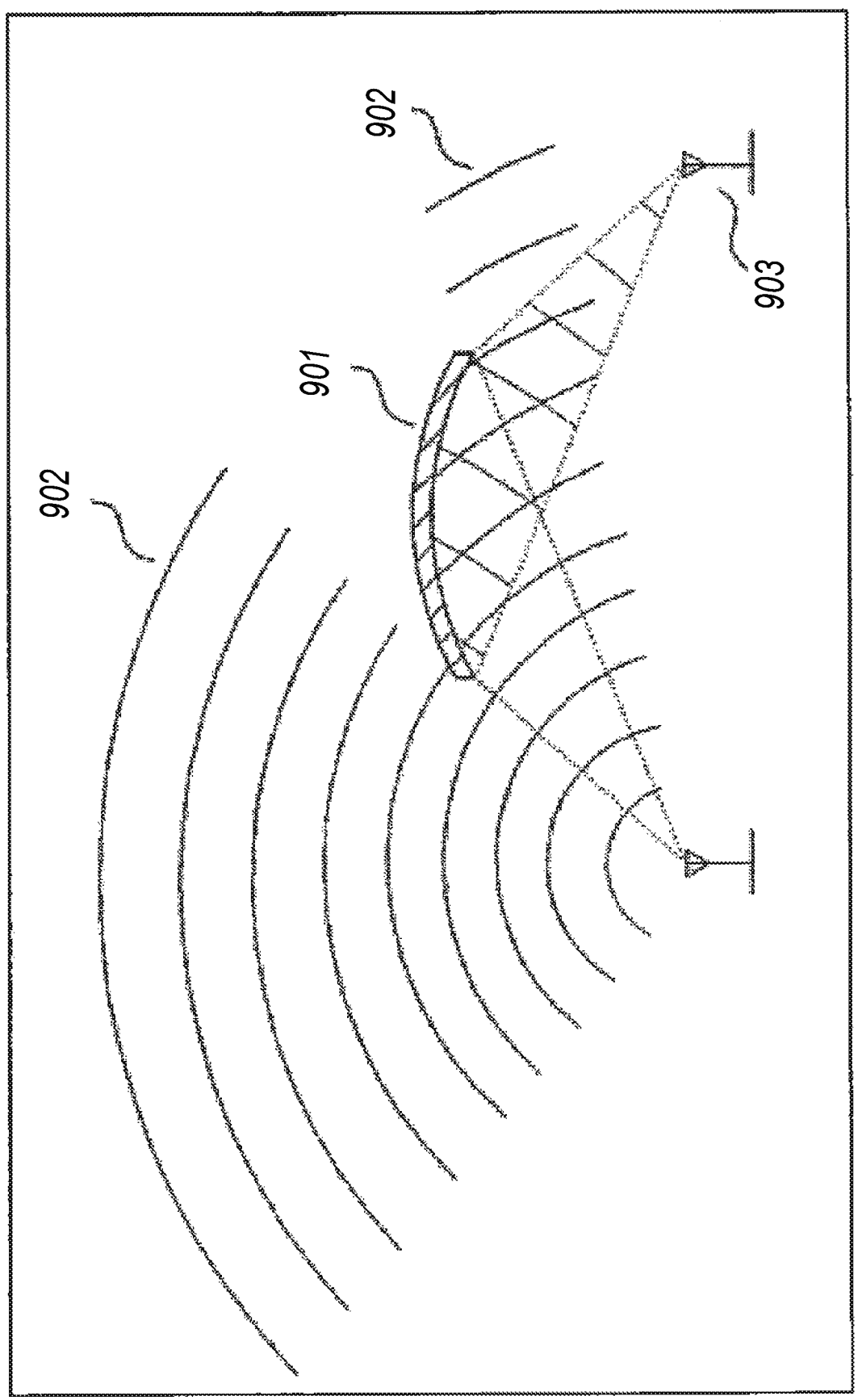
FIG. 9 illustrates a wear monitoring system having stationary sensors and reflectors in accordance with an exemplary embodiment.

FIG. 9 shows an example of a wear monitor system where the sensors and reflectors 901 are stationary with respect to each other. When the signal is transmitted, some of the signal bypasses the reflector and is lost 902. The RF wave also spreads as it moves. A parabolic reflector 901 is used to focus the reflections on the receiver 903. Before any wear of the reflector 901 commences, the signal levels will be the greatest at the receiver 903. As wear occurs, more of the RF signal will bypass the reflector 901. A properly designed reflector will still focus enough RF energy on the receiver to be detected when the maximum wear depth is reached. This signal amplitude at the receiver will indicate the progression of wear on the reflector, and thereby indicate the wear on the device being monitored.

Figure 10:
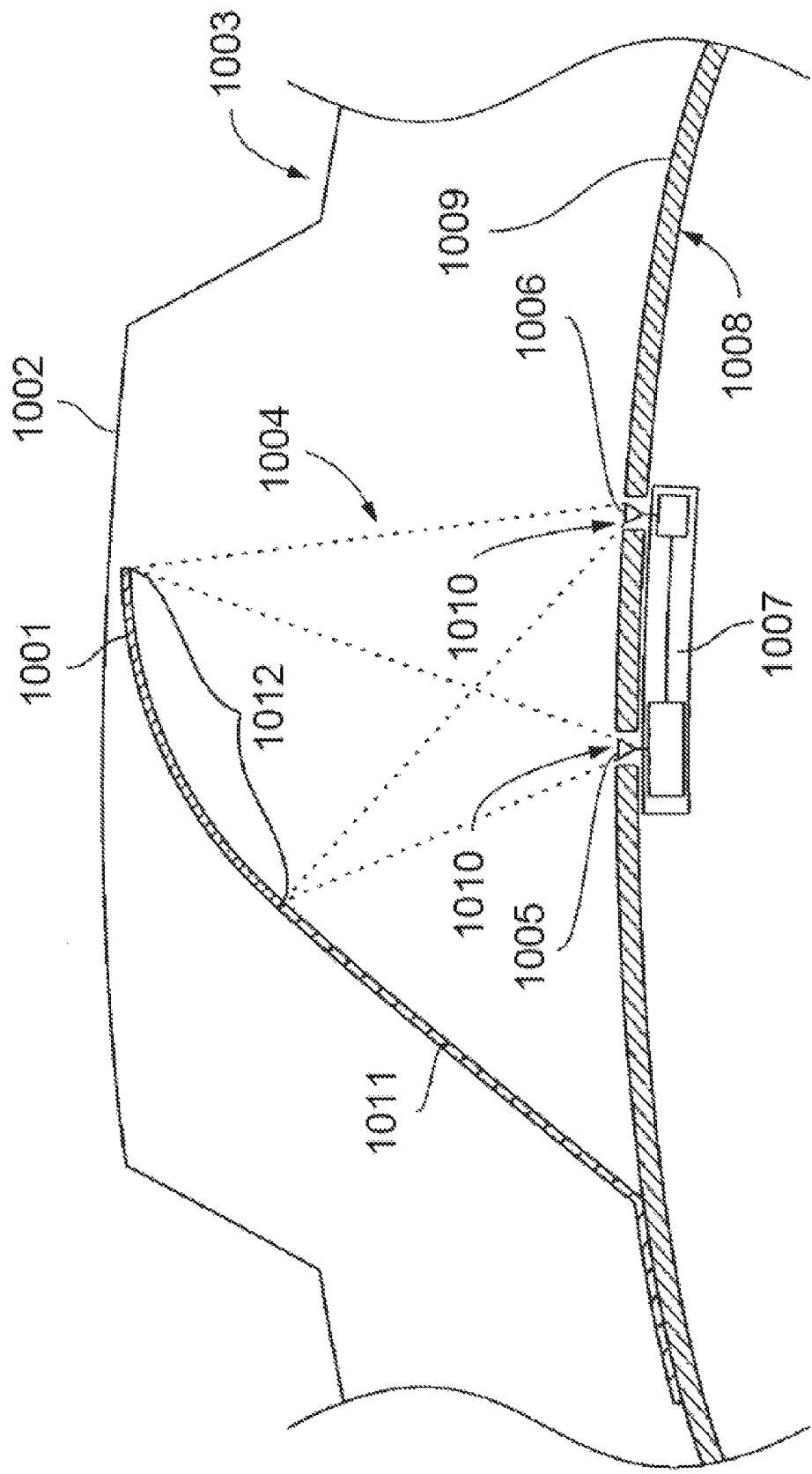
FIG. 10 illustrates an alternative embodiment for the physical implementation of a reflector tire wear sensor system.

Referring now to FIG. 10, there is shown an embodiment for the physical implementation of the sensor of FIG. 9 within a tire, slurry pipe liner, haul truck bed liner or hose. In this embodiment, the placement of the sensor within a tire tread is specifically described and, in similar fashion, may be used with the belts described above. As shown in FIG. 10, a metallic parabolic reflector 1001 is embedded in the tread 1002 of the tire 1003 and positioned in such a way as to reflect radio waves 1004 from a radio wave transmitter 1005 and focus the reflections to a radio wave receiver 1006. The transmitter 1005 and receiver 1006 are mounted to a PCB 1007 that is attached to the inside surface 1008 of a metal support ring 1009 within the tire 1003, beneath the tire tread 1002. Apertures 1010 are cut through the support ring 1009 to allow the transmission of radio waves 1004 between the transmitter 1005, the reflector 1001, and the receiver 1006. A bracket 1011 is attached to the reflector 1001 may be used to assist in positioning of the reflector 1001 within the tire tread 1002. As the tire tread 1002 wears, the arc length 1012 of the reflector 1001 decreases and the strength of the signal acknowledged by the receiver 1006 diminishes. The strength of the signal is therefore a function of the amount of tread wear. In similar fashion, parabolic reflectors may be utilized in conveyor and related belt systems.

Figure 11:
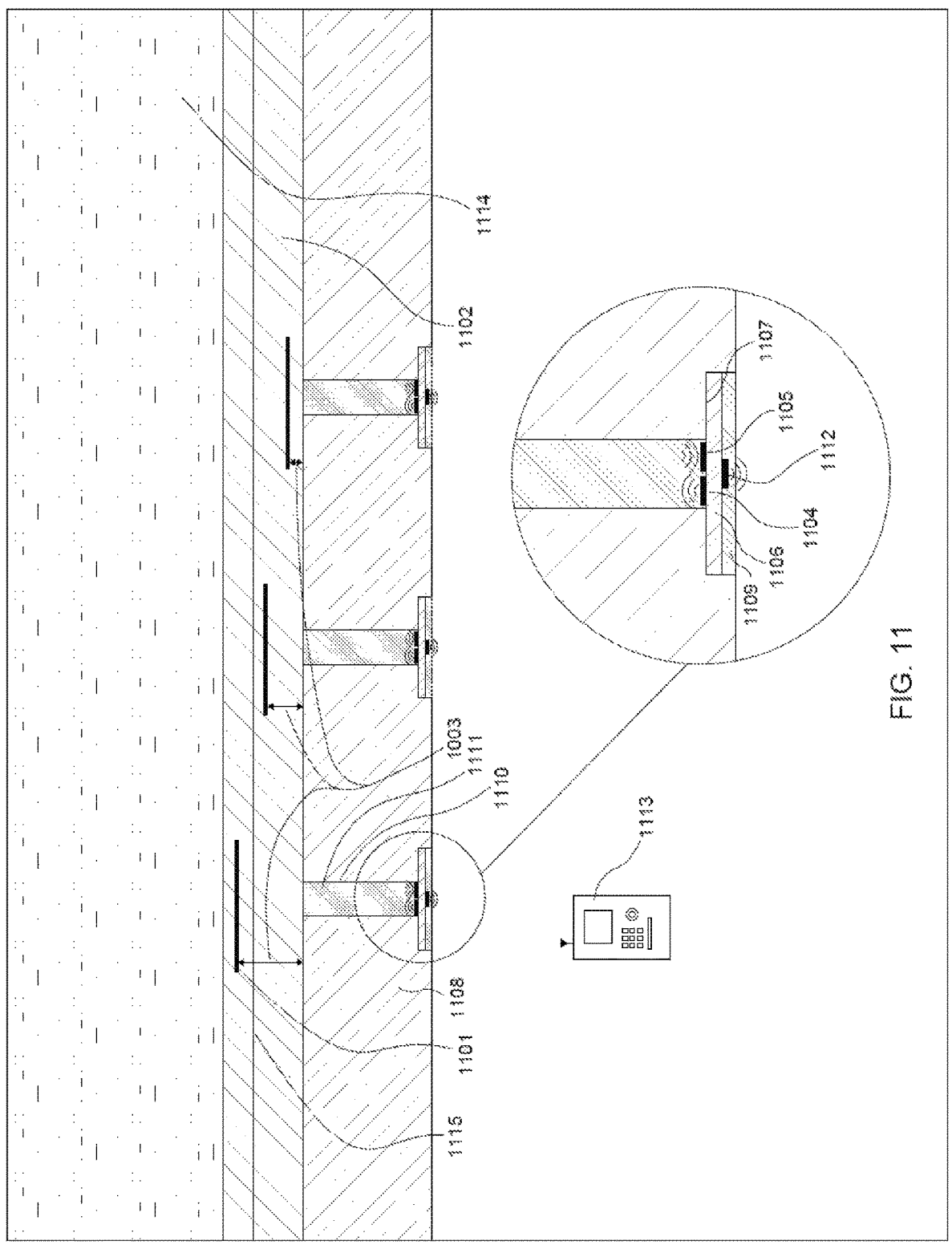
FIG. 11 illustrates an alternative embodiment for the physical implementation of a reflector slurry pipe liner wear sensor system.

Referring now to FIG. 11, a plurality of metallic reflectors 1101 are embedded in a slurry pipe liner 1102 for example at different depths 1103. Each reflector 1101 is associated with a transmitting antenna 1104 and a receiving antenna 1105. The transmitting 1104 and receiving antennas 1105 are in communication with a PCB 2006 that is mounted in a milled flat 1107 in the outer pipe wall 1108. The PCB 1106 may be protected by a material 1109 such as PTFE that allows penetration of a radio signal. The transmitting antenna 1104 transmits a radio signal through an aperture 1110 in the outer pipe wall 1108 in the direction of the reflector 1101. The aperture 1110 may be filled with a material 1111 such as PTFE that allows penetration of a radio signal. The radio signal reflects off of the reflector 1101 and is acknowledged by the receiving antenna 1105. The PCB 1106 stores the data from each set of reflector 1101 and antennas 1104 and 1105. The PCB 1106 is in communication with another transmitting antenna 1112 that transmits the information that is stored on the PCB 1106 to the outside of the pipe wall 1108 for upload to a mobile data acquisition device 1113 such as a handheld computer. The mobile data acquisition device 1113 may also act as the transmitter 1104 and receiver 1105. If the pipe liner 1102 containing slurry or other abrasive mixtures 1114 wears to a depth 1115 such that the reflector 1101 is lost, the receiving antenna 1105 will no longer realize the signal from the transmitting antenna 1104. This loss of signal indicates that the amount of wear associated with reflector depth 1103 has occurred. The transmitting antenna 1112 may be replaced with a wired connection to the data acquisition device 1113.

The same technique shown in FIG. 11 may be used to monitor wear in non-ferrous haul truck bed liners in the same manner described to monitor pipe liners 1102. In this embodiment, said pipe wall 1108 is a haul truck bed.

The same technique shown in FIG. 11 may also be used to monitor wear in hoses in the same manner described to monitor pipe liners 1102. In this embodiment, the pipe wall 1108 is absent and the PCB 1106 is mounted to the outside of the hose, represented in FIG. 11 by the pipe liner 1102.

Remote Recessed Reflector Antenna

In certain embodiments of the present disclosure, a Remote Recessed Reflector Antenna ($R^3A$) design that enables conductive and non-conductive surfaces to transmit information via, for example, a radio frequency antenna is used for data transmission. The $R^3A$ is recessed into at least one of the conductive and non-conductive surfaces such that surface topography is not affected. This is accomplished through the use of a recessed cavity that is covered with a dielectric material such as, for example, Polytetrafluoroethylene (PTFE) available under the name Teflon®. According to the exemplary $R^3A$ design, the surface is not functionally or aesthetically hindered by the presence of a radio transmitter and the transmitter is protected from the environment outside of a cavity in which the transmitter is recessed. In most prior-art arrangements, both the antenna and the antenna cover protrude from the surface. Objects that can host the $R^3A$ include, for example, flat and rounded surfaces that are traveled or subject to abrasion by the environment, or aerodynamic forces. The $R^3A$ design is mounted in the surfaces of the tire which are least exposed to abrasion, such as the metal support rings, henceforth referred to as "chassis," that are commonly embedded in the tire during manufacturing.

In other embodiments, data transmission may also be accomplished by the use of a conventional, non-recessed antenna if the surface it is mounted on is not subject to abrasion or other forces. The antenna may be encapsulated or otherwise covered with materials that will best withstand the abrasion. Teflon is an example of one material that may be well suited since Teflon has low surface friction; is rigid, and does not significantly attenuate radio frequency transmissions. Small gaps around covers made of materials such as PTFE, may be sealed from moisture using epoxy or other suitable sealants. The size of the aperture used for wireless transmission must be minimized to best protect the antenna and associated circuits. One or more antennas may be implemented for this application, based on the need to radiate and receive signals in multiple directions.

Figure 12:
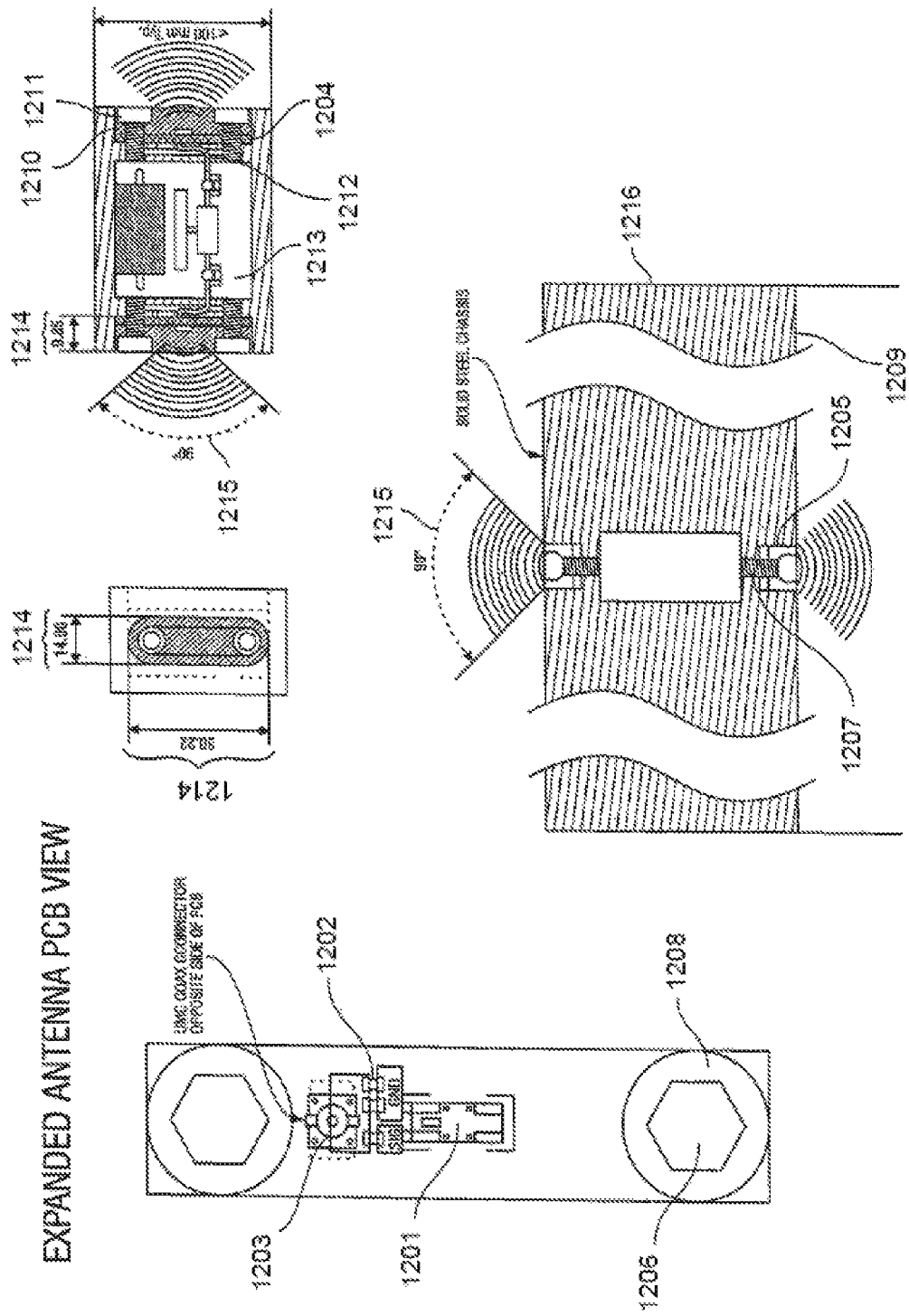
FIG. 12 illustrates a transmission system using remote dual antennas with recessed reflectors.

FIG. 12 illustrates a transmission system using remote dual antennas with recessed reflectors in accordance with an exemplary embodiment. An antenna 1201, series and shunt tuning components 1202 and a cable connector 1203 are mounted on a circuit board 1204 that is positioned in an antenna cavity 1205 with two mounting holes 1206 aligned with threaded screw holes 1207 in a bottom region of the antenna cavity 1205. The bottom sides of the two screw holes 1206 in the circuit board 1204 have exposed annular rings 1208 that are conductively bonded to a steel surface of the bottom region of the cavity 1205 using an electrically-conductive compound. This conductive joint between a grounded circuit board 1204 annular rings 1208 extends the circuit board 1204 ground plane into a steel chassis 1216. This overall ground plane acts as the reflector for the antenna. Currently, the antennas are mounted on the edges of flat corner surface reflectors. Mounting the antenna 1201 on flat surface corner reflectors is not possible because the surfaces 1209 are 'wear-surfaces' (the antenna 1201 would be immediately destroyed) and the surfaces are contoured such that they have no corners. Recessing the antenna 1201 into the surface prevents it from being destroyed by compression forces and abrasion in the tire.

The antenna 1201 and the circuit board 1204 are further protected with a cover 1210 formed of a material such as Teflon that fills the cavity 1205 in front of the antenna 1201 and that is attached by means of two screws 1211. Connectors 1203 are attached to RF cables 1212. RF cables 1212 carry signals to and from the transceiver and processing circuit board 1213. Dimensions of cavity 1214 allow the radiation pattern 1215 to be ninety degrees (or greater, by means of altering these dimensions 1214, when practical). This set of cavity dimensions 1214 is specific to this example and may be altered, as required, for similar embodiments of this disclosure.

Redundant Transceiver Wear Sensor for Non-Ferrous Material Wear Sensing

Figure 13:
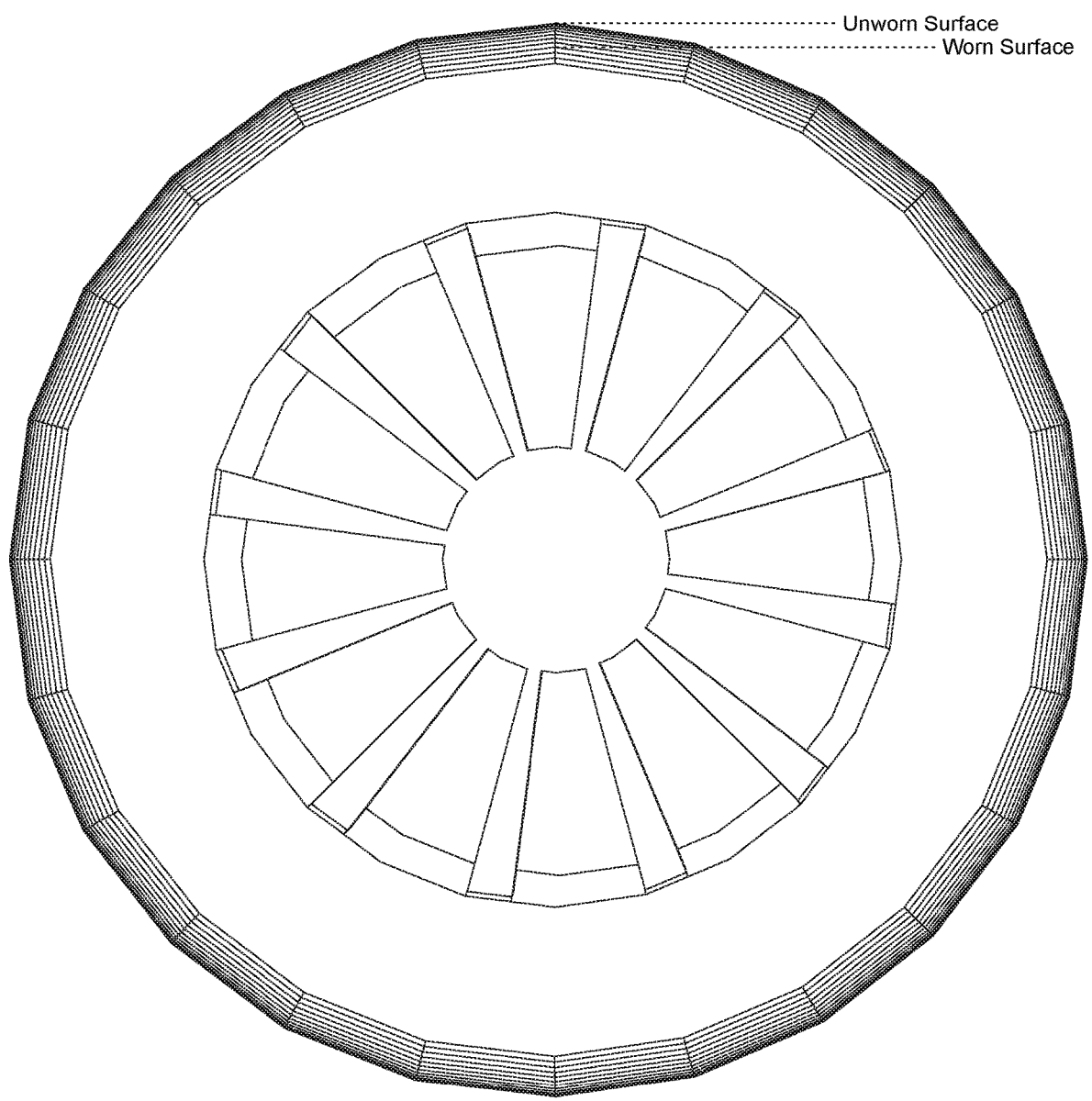
FIG. 13 illustrates the wear path of a tire.

FIG. 13 illustrates a wear-path of a tire. The wear-path is defined as the path from a surface of a new tire to a wear-out or damage limit that is to be monitored. Exemplary embodiments disclose a novel Redundant Transceiver Tire Wear Sensor with Remote Recessed Reflector Antenna (RTTWS-$R^3A$) design that enables tires to automatically report wear, tear or rupture status over their life-cycle. This disclosure is, however, not limited to use in tires and may be utilized in any equipment that has wear surfaces that may benefit from wear monitoring.

In a typical embodiment, the RTTWS-$R^3A$ implementation process begins by defining the wear paths on tires that are to be monitored. Since each tire has unique characteristics, the wear-paths to be monitored differ in both location and wear depth. Wear rate at different points on the tires may vary based on the tires engagement with a ground surface. For example, a small tire may only require one wear-path to be monitored while larger tires may require multiple paths or wear-depths (i.e., distance from new surface to wear-out limit) to be monitored. According to exemplary embodiments, wear depth monitoring is accomplished for each wear-path by embedding, for example, transducers at intervals along the wear-path. As tire surfaces wear reaches a transducer, its characteristics are altered. According to exemplary embodiments, the RTTWS-$R^3A$ implementation process includes any type of transducer to detect wear on the tire. The use of resistors as transducers is given here as an example. As a tire rotates, the part of the tire that contacts the road surface may deflect due to the weight of the vehicle. Such deflection could cause the alignment of the transducers, and particularly the parabolic reflectors, to deviate enough to cause an error in the wear-depth calculation. To prevent this, an accelerometer is used to determine the position of the tire with respect to the road surface. Signals are sampled with the wear area to be sampled is not in contact with the road surface.

Figure 14:
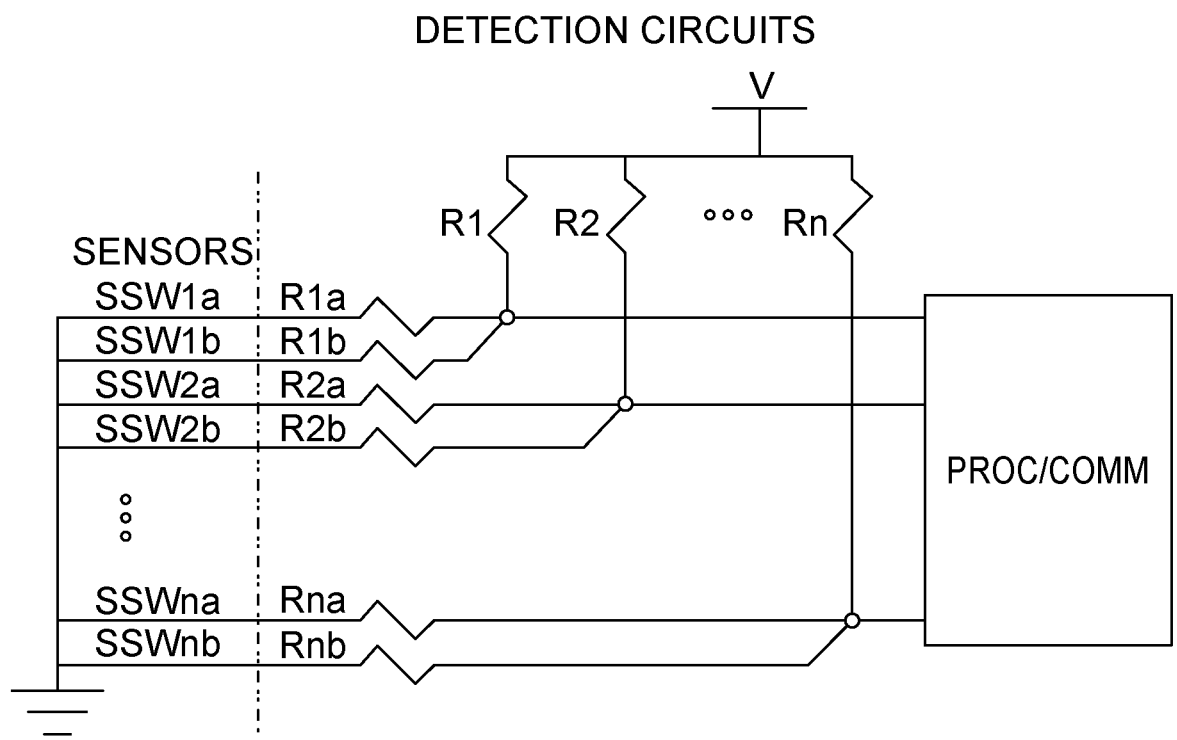
FIG. 14 illustrates a wear path monitoring circuit in accordance with an exemplary embodiment.

FIG. 14 illustrates a wear path monitoring circuit in accordance with an exemplary embodiment. Although this application is not limited to a specific type of transducer, the use of stainless steel wires and resistor pairs (i.e., redundant resistors) for monitoring is disclosed herein as an example. A first wire pair SSW1a/SSW1b is embedded nearest an outer wear surface. Additional wire pairs SSW2a/SSW2b through SSWna/SSWnb are equally spaced apart along the wear path. When a tire surface wears down or is damaged to a wire in a pair such as, for example, the wire pair SSW2a/SSW2b, the combinatorial resistance changes. The change in resistance indicates to a processing device that the wear depth for the wire pair has been reached. In a typical embodiment, the processing device may be, for example, a computer, a processor, a microcontroller, and the like. Although not shown in the wear path monitoring circuit, the redundancy may be increased, from pairs to groups, by adding more wires. This will decrease the probability of false indications due to defective wire failures. More redundancy may be added by independently returning ground wires to the circuit board independently.

According to exemplary embodiments, the use of redundant transducers and traces improve the monitoring reliability of the sensors. Single component, connection or trace failures resulting from defects in manufacturing, temperature extremes, shock or vibration of the operating environment are detected and compensated for in the processing circuitry. For example, if R1a and R1b are the same value and the parallel combination of R1a and R1b through wire pair SSW1a/SSW1b equals the value of R1, the analog voltage detected at the an input of the processing device is V/2. If a failure of wire SSW1a or wire SSW1b or a connection or wiring to either of these resistors results, due to a manufacturing, material fault, temperature extremes, shock or vibration, one of the resistors will be omitted from the circuit. This will result in the resistance of R1 being ½ the resistance of the remaining connected resistor (R1a or R1b). The voltage detected at the input will then be V/3. This voltage level will indicate to the processor that the failure may not be related to wear. If the voltage level is due to wear, it will not make a difference. The other wire in the pair will soon be removed by wear. Until both wires in the pair are faulted, the wear-point will not be considered to have been reached. In sensors that do not have redundancy, failures in any of the traces or transducer would incorrectly indicate that the wear point was reached.

Figure 15A:
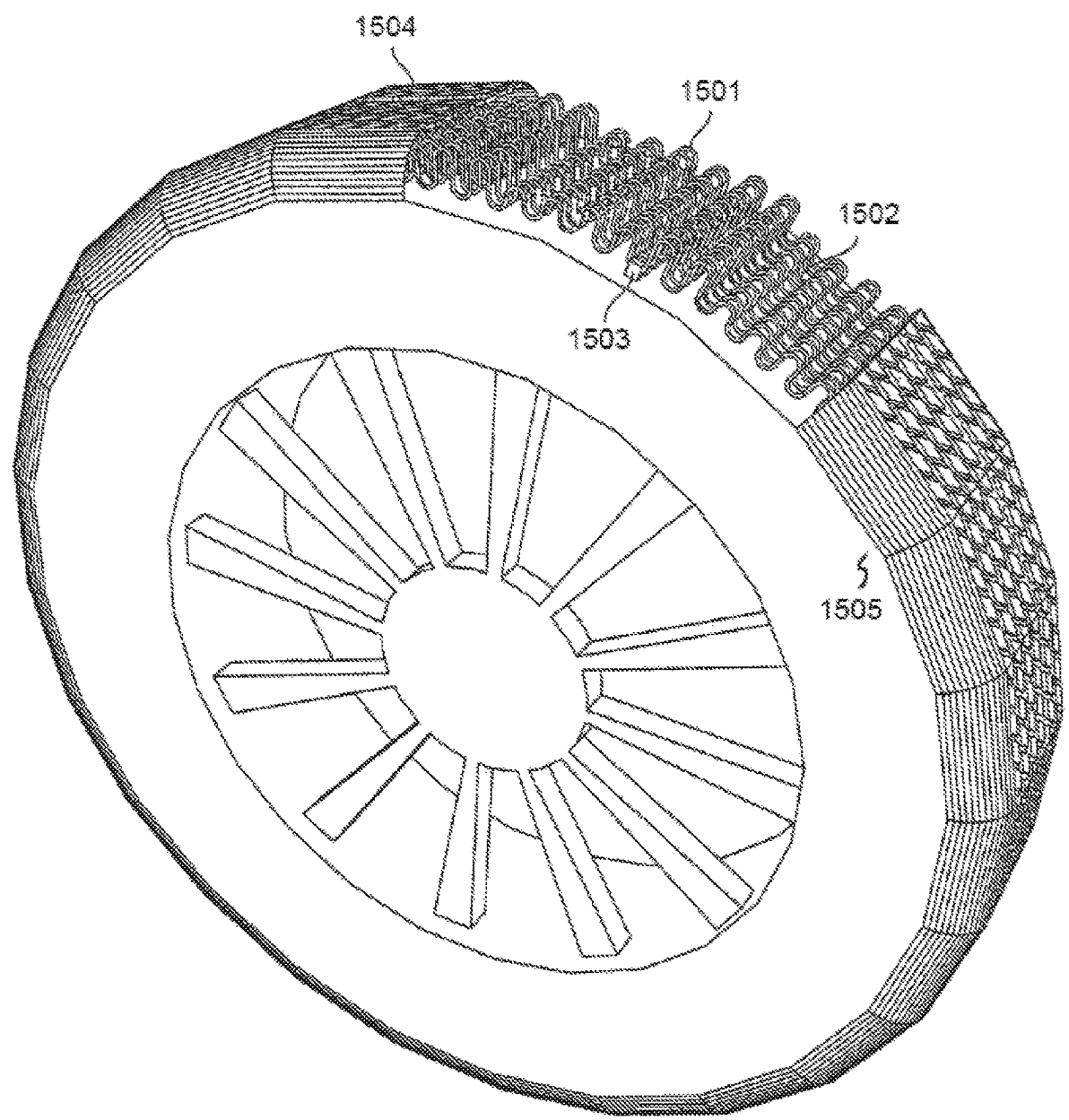
FIG. 15A-15C illustrate physical implementation of the sensors within the tire in accordance with the embodiment of FIG. 14.
Figure 15B:
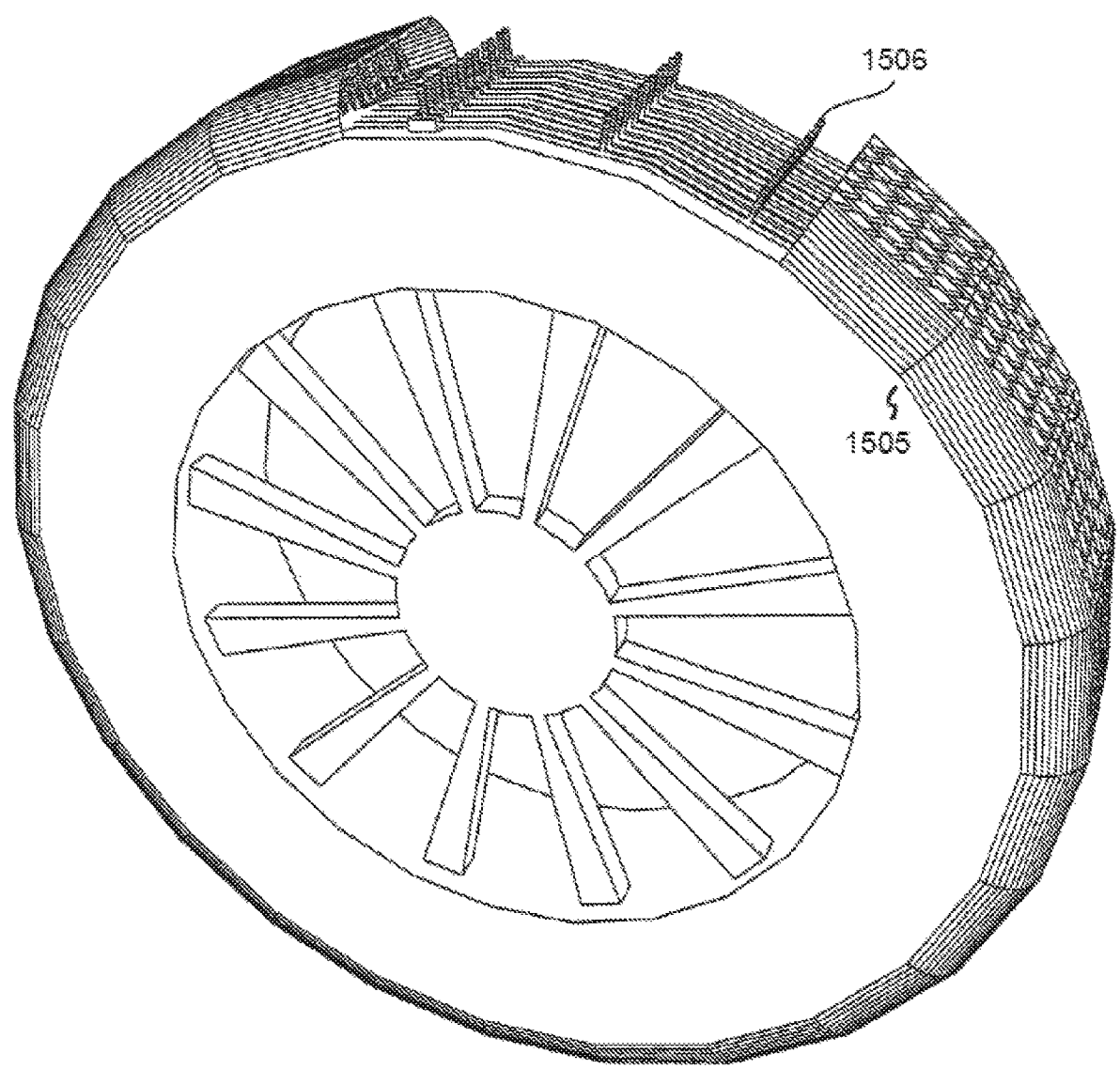
Figure 15C:
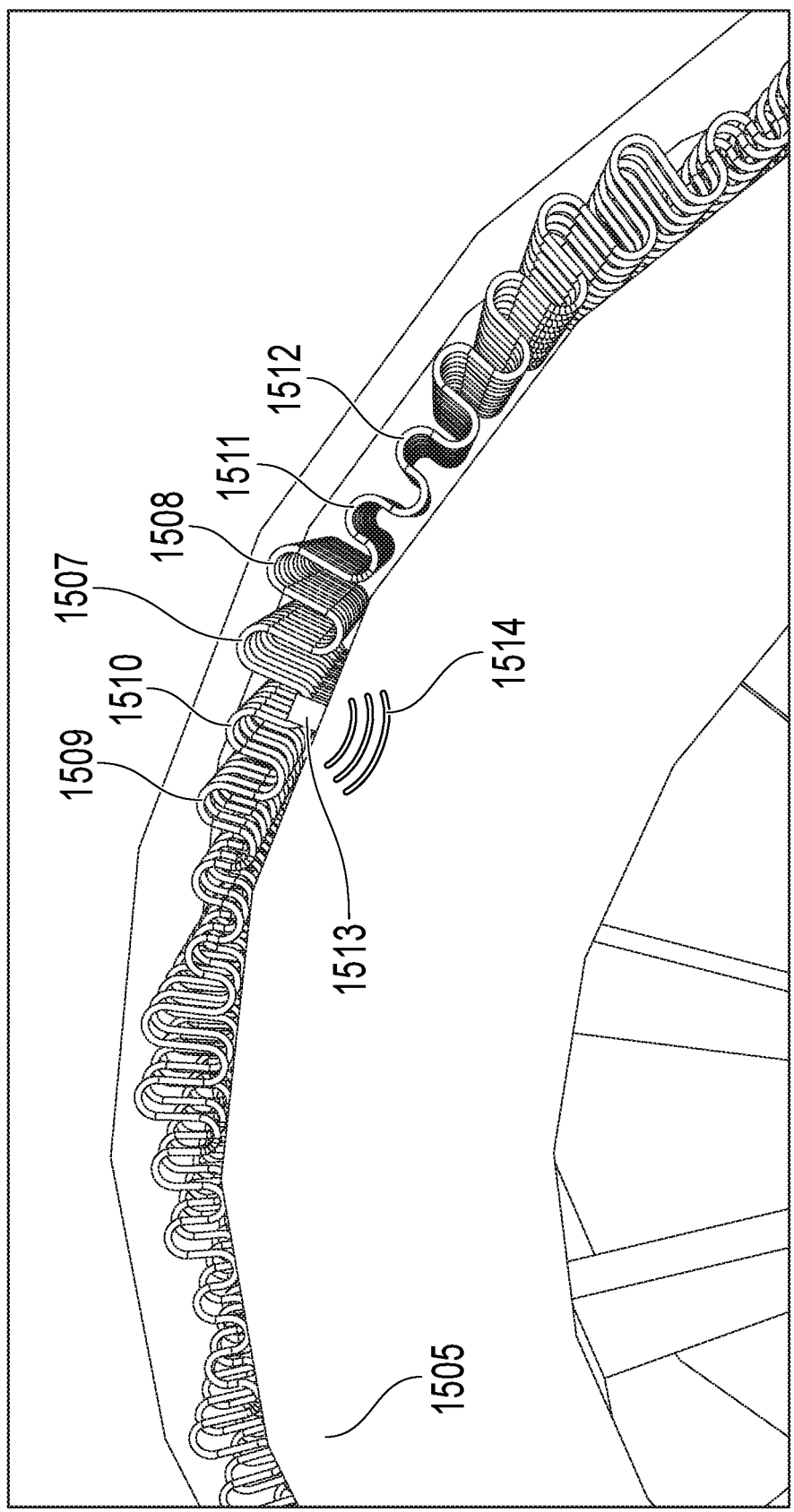

FIG. 15A-15C illustrate physical implementation of the sensors within the tire in accordance with an exemplary embodiment. The physical implementation of the sensor wires 1501 and communication wires 1502 may be accomplished by embedding the sensor wires 1501 and the communication wires 1502 in the tread during a vulcanization process. A communication element 1503 may be installed in a tire 1504 inside of a tire componentry such as, for example, a chassis 1505 during a manufacturing process, prior to vulcanization, or optionally outside of the tire componentry in the tread during the vulcanization process. The physical paths of the circuitry and communication cable may be perpendicular 1506 to the chassis 1505 and/or at an angle to the chassis 1505. In some embodiments, the tire 1504 may be embedded with a single wire pair. In other embodiments, the tire 1504 may be embedded with multiple wire pairs. For exemplary illustration, numerous wire pairs are shown in FIG. 15A-15B.

The redundant wire pairs SSW1a 1507, SSW1b 1508, SSW2a 1509, SSW2b 1510, SSWna 1511 and SSWnb 1512 are shown with an exaggerated scale and layout in a small segment of a tire. Wires are routed within the tread such that the steel flexes within its elastic limits to avoid metal fatigue, allowing the wires to remain intact until they are broken by tire wear. All sensor wires route to processing element 1513. In a typical embodiment, data is formed into packets and transmitted wirelessly 1514 inward towards at least one of a center of the tire, outward from the center of the tire, or radially out of the tire, to a host which is generally located on a vehicle. FIG. 15A-15C illustrate three different depths of wire sensors. Exemplary embodiments disclose implementations from one sensor wire pair to any number or wear depths and sensor array configurations.

Figure 16:
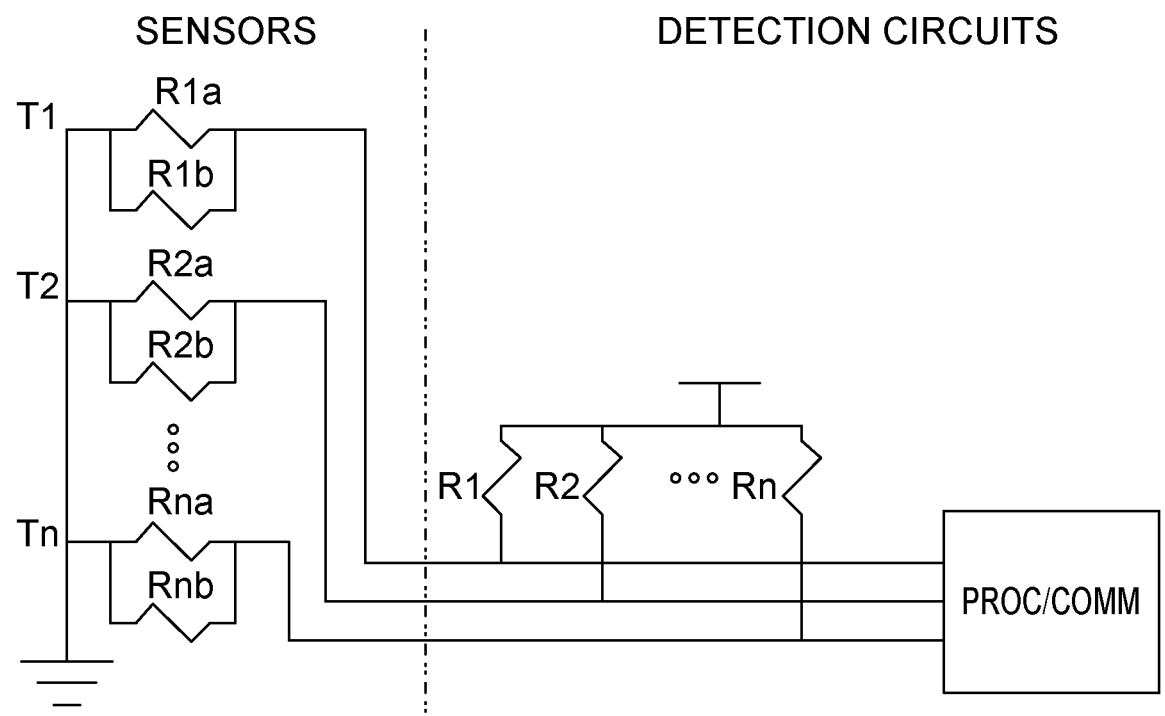
FIG. 16 illustrates an alternative embodiment of a wear path monitoring circuit.

FIG. 16 illustrates a wear path monitoring circuit in accordance with an alternate embodiment using resistor pairs (i.e., redundant resistors). T1 is embedded nearest an outer wear surface with T2 through Tn equally spaced along the wear path. Tn is located closest to the wear limit. When a tire surface wears down to a resistor pair such as, for example, R1a and R1b, the combinatorial resistance changes. The resistance can be reduced or shorted (if filled with mud) or increased or open (if the connections or resistor are damaged or broken). The change in resistance indicates to the processing device that the wear depth for the resistor pair has been reached. Although not illustrated, the traces may also be made redundant by use of more traces installed on flexible circuit board layers to decrease the probability of false indications due to faulty trace failures.

Redundant transducers and traces improve monitoring reliability of the sensors. Single component, connection or trace failures resulting from defects in manufacturing, extremes in temperature, shock or vibration of the operating environment are detected and compensated for in the processing circuitry. For example, if the parallel combination of R1a and R1b equals the value of R1, the analog voltage detected at the processor input is V/2. If a failure of R1a, R1b or a connection or trace path to either of these resistors results, due to a manufacturing fault, temperature extremes, shock, or vibration, one of the resistors is omitted from the circuit. This results in the resistance of R1 being ½ the resistance of the remaining connected resistor such as, for example, R1a or R1b. The voltage detected at the input will then be V/3. This voltage level will indicate to the processing circuitry that the failure may not be related to wear. If the voltage level is due to wear, it will not make a difference. The other resistor will soon be removed by wear. Until both resistors in the pair are faulted, the wear-point will not be considered to have been reached. In sensors that do not have redundancy, failures in any of the traces or transducer will incorrectly indicate that the wear point was reached.

Figure 17B:
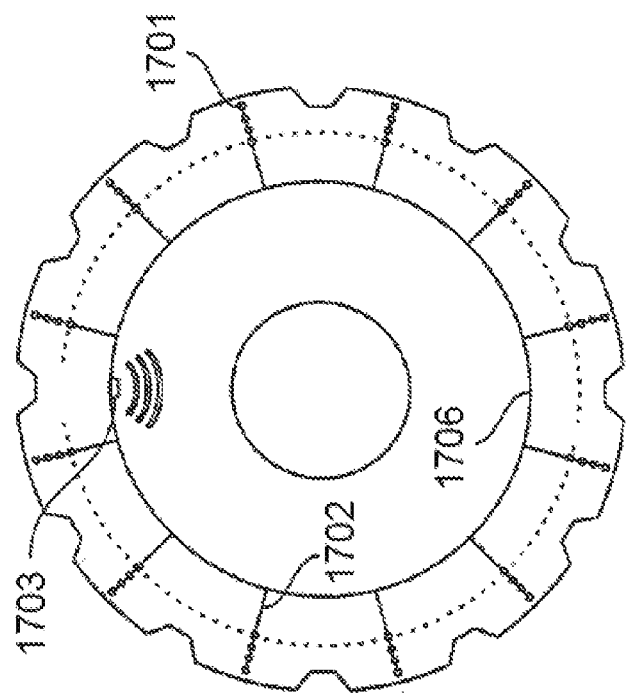
FIG. 17A-17C illustrate physical implementation of the sensors within the tire in accordance with the embodiment of FIG. 16.
Figure 17A:
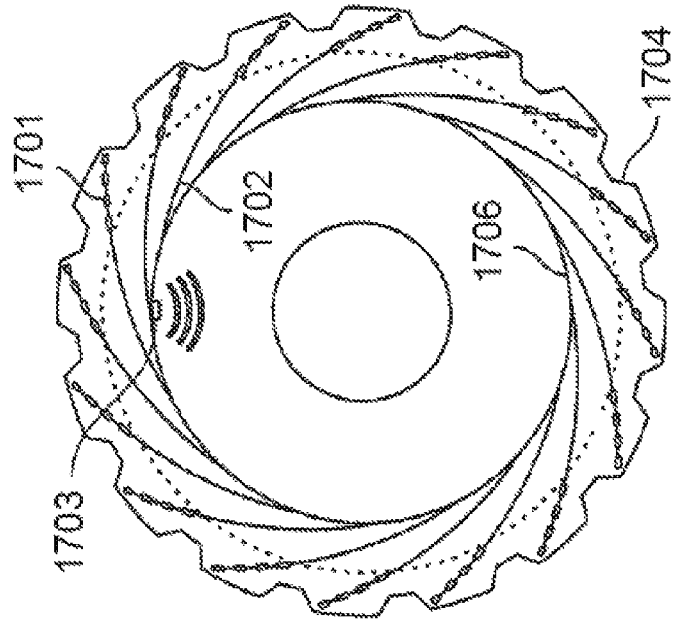
Figure 17C:
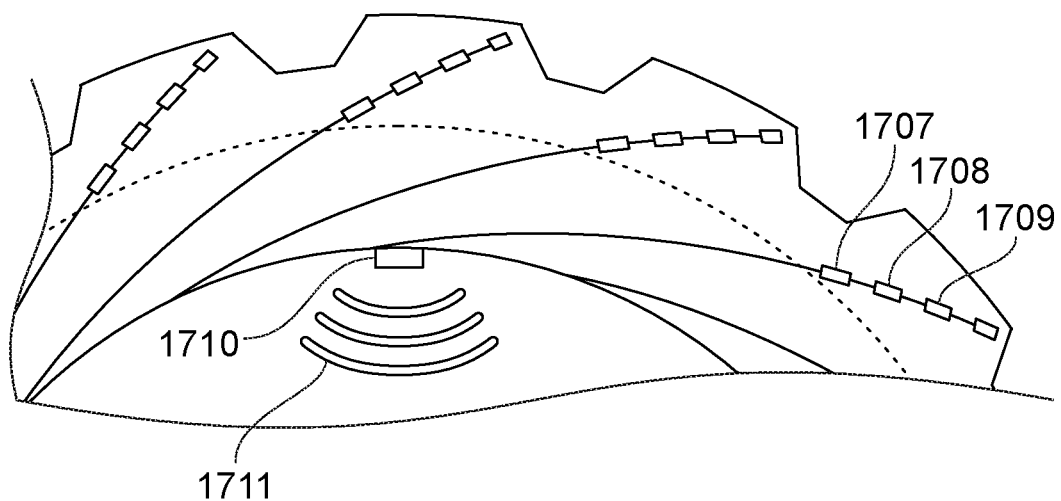

FIG. 17A-17C illustrate physical implementation of the sensors within the tire in accordance with an alternate embodiment. The physical implementation of the sensor wires 1701 such as, for example, wires and redundant resistor pairs imbedded in flexible PCB and communication wires 1702 to the processing and communication element 1703 may be accomplished by embedding them in the tread during the vulcanization process as is presently done with RFID circuitry. The processing and communication element 1703 may be installed inside the tire component surfaces 1706 (e.g., the "chassis") during the manufacturing process prior to vulcanization, or outside of the tire componentry (the "chassis") and in the tread 1704 and installed during the vulcanization process. The physical paths of the circuitry and communication cable may be perpendicular to 1706 and/or at an angle to the chassis 1706.

The transducers T1 1707, T2 1708, and Tn 1709 are shown with exaggerated scale and layout in a small segment of a tire. Wires are routed within the tread to redundant resistors on flexible PCB such that the steel and PCB flexes within its elastic limits to avoid metal fatigue, allowing the wires and PCB mounted resistors to remain intact until they are broken by tire wear. All sensor wires route to processing element 1710 which can be mounted in the tread during the vulcanization process, or outside of the tread as shown. The data is formed into packets and transmitted wirelessly 1711 inward towards the center of the tire and/or outward from the center of the tire or radially out of the tire to the host which is generally located on the vehicle. The diagram shows 4 different depths redundant wear sensors. Exemplary embodiments disclose implementations from one sensor pair to any number or wear depths and sensor array configurations.

From the perspective of monitoring the wear of a tire, since there are no practical means of attaching wires from the tire to the vehicle for communication, the application is considered to be remote. The monitoring electronics are embedded in the rotating tire. Sending the signals to the operator is a challenge. For the tire, the monitoring electronics inside the tire are powered by a battery. These batteries are to be specified to operate the monitoring circuits for the lifetime of the tire. When the tire is installed on the machine, the monitoring processor may be activated (awakened) from a 'deep sleep' mode and remains active for the life of the tire or may only be active when the tire rotates.

Referring now to power aspects for the embodiments shown and described herein, the use of a battery with the methods and systems of the present disclosure is optional if piezoelectric ceramic wafers (PCW's) are implemented into the circuitry. PCW's develop small voltages when they are subjected to vibrations that excite them to move at their resonant frequencies. State of the art devices have now been developed to convert these small voltages into energy sufficient to power small sensors and transmitters. This type of technology is being called "energy harvesting". The currents harvested from these devices are used to charge electrical storage devices such as capacitors, super capacitors and potentially batteries. When sufficient energy has been stored to read the transducers and transmit the data in a wireless packet, the data is transmitted to the host. This disclosure may be applied to tire wear monitoring using the tire rotation and vibration to excite the PCW.

General Computing and Computer Programming Disclosure

Particular embodiments may include one or more computer-readable storage media implementing any suitable storage. In particular embodiments, a computer-readable storage medium implements one or more portions of the processor, one or more portions of the system memory, or a combination of these, where appropriate. In particular embodiments, a computer-readable storage medium implements RAM or ROM. In particular embodiments, a computer-readable storage medium implements volatile or persistent memory. In particular embodiments, one or more computer-readable storage media embody encoded software.

In this patent application, reference to encoded software may encompass one or more applications, bytecode, one or more computer programs, one or more executables, one or more instructions, logic, machine code, one or more scripts, or source code, and vice versa, where appropriate, that have been stored or encoded in a computer-readable storage medium. In particular embodiments, encoded software includes one or more application programming interfaces (APIs) stored or encoded in a computer-readable storage medium. Particular embodiments may use any suitable encoded software written or otherwise expressed in any suitable programming language or combination of programming languages stored or encoded in any suitable type or number of computer-readable storage media. In particular embodiments, encoded software may be expressed as source code or object code. In particular embodiments, encoded software is expressed in a higher-level programming language, such as, for example, C, Python, Java, or a suitable extension thereof. In particular embodiments, encoded software is expressed in a lower-level programming language, such as assembly language (or machine code). In particular embodiments, encoded software is expressed in JAVA. In particular embodiments, encoded software is expressed in Hyper Text Markup Language (HTML), Extensible Markup Language (XML), or other suitable markup language.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, the processes described herein can be embodied within a form that does not provide all of the features and benefits set forth herein, as some features can be used or practiced separately from others. The scope of protection is defined by the appended claims rather than by the foregoing description. All changes which come within the meaning and range of equivalency of the claims are to be embraced within their scope.

The invention claimed is:

1. A system for wear monitoring, comprising:
a moving non-metallic surface, the moving non-metallic surface comprising artifacts comprising joining or structural reinforcing metallic elements;
integrated metallic shapes embedded at pre-determined depths in the moving non-metallic surface;
stationary focused radio-wave transmitters positioned on a first side of the moving non-metallic surface and transmitting focused radio frequencies;
stationary focused radio-wave receivers positioned on a second opposite side of the moving non-metallic surface;
wherein the moving non-metallic surface, the artifacts, and the integrated metallic shapes produce a signature of the radio waves transmitted by the stationary focused radio-wave transmitters along an entire length and breadth of the non-metallic surface; and
wherein detection of the signature of the radio waves from the stationary focused radio-wave transmitters by the stationary focused radio-wave receivers is averaged over time to map a condition of the moving non-metallic surface to infer wear.

2. The system for wear monitoring of claim 1 wherein the stationary focused radio wave receivers detect the radio wave signatures of the integrated metallic shapes where the moving non-metallic surface is prone to wear to identify the degree of change in the size or the presence of the integrated metallic shapes over time and therefore the degree of wear of the moving non-metallic surface.

3. The system for wear monitoring of claim 1 wherein the integrated metallic shapes are embedded in the moving non-metallic surface in areas of the moving non-metallic surface that are not prone to wear for use as identification codes to a reference position and for tracking of at least one of changes in lateral position and excessive vibration, linear speed, damage, and stretch of the moving non-metallic surface.

4. The system for wear monitoring of claim 1 wherein the stationary focused radio wave receivers detect radio wave signatures of the artifacts for identification of reference position and for tracking of at least one of changes in lateral position, excessive vibration, linear speed, damage, and stretch of the moving non-metallic surface.

5. The system for wear monitoring of claim 1 wherein:
the stationary focused radio wave receivers detect attenuation of the focused radio waves through the moving non-metallic surface; and
a degree of change in the attenuation of the focused radio waves through the moving non-metallic surface over time is averaged to map the condition of the moving non-metallic surface to infer wear.

6. The system for wear monitoring of claim 1 wherein the stationary focused radio receivers do not detect any radio wave signatures from artifacts, the integrated metallic shapes, or the moving non-metallic surface, indicating that the moving non-metallic surface is at least one of separated, torn, or damaged.

7. The system for wear-monitoring of claim 1 wherein the integrated metallic shapes are at least one of parabolic, round, and rectilinear.

8. The system for wear-monitoring of claim 1 wherein the integrated metallic shapes are at least one of installed during a manufacturing process of the moving non-metallic surface, and installed at any time following the manufacturing process.

9. The system for wear-monitoring of claim 1 wherein the moving non-metallic surface is a conveyor belt.

10. The system for wear-monitoring of claim 1 wherein the moving non-metallic surface is a serpentine belt.

11. A system for wear monitoring, comprising:
a moving non-metallic surface, the moving non-metallic surface comprising artifacts comprising fabricated with joining or structural reinforcing metallic elements;
integrated metallic shapes embedded at pre-determined depths in the moving non-metallic surface;
stationary focused radio-wave transmitters positioned on a first side of the moving non-metallic surface and transmitting focused radio frequencies;
stationary focused radio-wave receivers positioned on the first side of the moving non-metallic surface;
wherein the moving non-metallic surface, the artifacts, and the integrated metallic shapes produce a signature of the radio waves transmitted by the stationary focused radio-wave transmitters along an entire length and breadth of the non-metallic surface; and
detection of the signature of the radio waves from the focused stationary radio-wave transmitters by the focused stationary radio-wave receivers is averaged over time and maps a condition of the moving non-metallic surface to infer wear.

12. The system for wear monitoring of claim 11 wherein the stationary focused radio wave receivers detect the radio wave signatures of the integrated metallic shapes where the moving non-metallic surface is prone to wear to identify the degree of change in the size or the presence of the integrated metallic shapes over time and therefore the degree of wear of the moving non-metallic surface.

13. The system for wear monitoring of claim 11 wherein the integrated metallic shapes are embedded in the moving non-metallic surface in areas of the moving non-metallic surface that are not prone to wear for use as identification codes to reference a position and for tracking of at least one of changes in lateral position and excessive vibration, linear speed, damage, and stretch of the moving non-metallic surface.

14. The system for wear monitoring of claim 11 wherein the stationary focused radio wave receivers detect radio wave signatures of the artifacts for identification of reference position and for tracking changes of at least one of lateral position, excessive vibration, linear speed, damage, and stretch of the moving non-metallic surface.

15. The system for wear monitoring of claim 11 wherein the stationary focused radio receivers do not detect any radio wave signatures from artifacts, the integrated metallic shapes, or of the moving non-metallic surface, indicating that the moving non-metallic surface is not physically present, is separated, torn, or damaged.

16. The system for wear-monitoring of claim 11 wherein the integrated metallic shapes are at least one of parabolic, round, and rectilinear.

17. The system for wear-monitoring of claim 11 wherein the integrated metallic shapes are at least one of installed during a manufacturing process of the moving non-metallic surface, and installed at any time following the manufacturing process.

18. The system for wear-monitoring of claim 11 wherein the moving non-metallic surface is a conveyor belt.

19. The system for wear-monitoring of claim 11 wherein the moving non-metallic surface is a serpentine belt.

* * * * *